United States Patent
Blancke et al.

(10) Patent No.: US 10,537,684 B2
(45) Date of Patent: Jan. 21, 2020

(54) ASSEMBLY FOR A DRUG DELIVERY DEVICE

(71) Applicant: Sanofi-Aventis Deutschland GmbH, Frankfurt am Main (DE)

(72) Inventors: Stefan Blancke, Frankfurt am Main (DE); Axel Teucher, Frankfurt am Main (DE); Michael Jugl, Frankfurt am Main (DE); Christiane Schneider, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 588 days.

(21) Appl. No.: 15/037,339

(22) PCT Filed: Nov. 17, 2014

(86) PCT No.: PCT/EP2014/074708
§ 371 (c)(1),
(2) Date: May 18, 2016

(87) PCT Pub. No.: WO2015/074982
PCT Pub. Date: May 28, 2015

(65) Prior Publication Data
US 2016/0287799 A1 Oct. 6, 2016

Related U.S. Application Data

(60) Provisional application No. 61/907,724, filed on Nov. 22, 2013.

(30) Foreign Application Priority Data

Apr. 24, 2014 (EP) .................................. 14165751

(51) Int. Cl.
*A61M 5/315* (2006.01)
*A61M 5/32* (2006.01)
*A61M 5/31* (2006.01)

(52) U.S. Cl.
CPC ...... *A61M 5/31513* (2013.01); *A61M 5/3158* (2013.01); *A61M 5/31543* (2013.01);
(Continued)

(58) Field of Classification Search
CPC .......... A61M 5/31513; A61M 5/31543; A61M 5/31551; A61M 5/3158; A61M 5/3202;
(Continued)

(56) References Cited

U.S. PATENT DOCUMENTS

| 533,575 A | 2/1895 | Wilkens |
| 4,865,591 A * | 9/1989 | Sams ................ A61M 5/31553 604/186 |

(Continued)

FOREIGN PATENT DOCUMENTS

| CN | 101600468 | 12/2009 |
| EP | 0295075 A1 | 12/1988 |

(Continued)

OTHER PUBLICATIONS

International Search Report and Written Opinion in International Application No. PCT/EP2014/074708, dated Apr. 8, 2015, 8 pages.

(Continued)

*Primary Examiner* — Jenna Zhang
(74) *Attorney, Agent, or Firm* — Fish & Richardson P.C.

(57) ABSTRACT

An assembly for a drug delivery device is presented. The assembly comprises a housing and a piston rod having a longitudinal axis, a distal end and a proximal end. The piston rod further comprises a piston rod interaction feature, and a piston rod guide being movable with respect to the piston rod, the piston rod guide further comprising a guide inter- (Continued)

action feature corresponding to the piston rod interaction feature, the piston rod guide being movable with respect to the piston rod to switch between a first state and a second state of the assembly, the second state being different from the first state. The assembly is configured such that, in a first state of the assembly, the piston rod guide is in a first axial position relative to the piston rod in which the piston rod interaction feature is arranged to interact with the guide interaction feature to prevent proximal movement of the piston rod with respect to the housing, and wherein, in a second state of the assembly being different from the first state, the piston rod guide is in a second axial position relative to the piston rod, the second axial position being different from the first axial position, wherein, in the second axial position, the piston rod interaction feature and the guide interaction feature are arranged such that proximal movement of the piston rod with respect to the housing is allowed.

20 Claims, 12 Drawing Sheets

(52) U.S. Cl.
CPC ...... *A61M 5/31551* (2013.01); *A61M 5/3202* (2013.01); *A61M 5/3146* (2013.01); *A61M 5/31585* (2013.01); *A61M 2005/3126* (2013.01)

(58) Field of Classification Search
CPC ............ A61M 5/3146; A61M 5/31585; A61M 2005/3126
See application file for complete search history.

(56) References Cited

U.S. PATENT DOCUMENTS

| | | | |
|---|---|---|---|
| 4,936,833 A * | 6/1990 | Sams ................ | A61M 5/31553 222/391 |
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,820,602 A * | 10/1998 | Kovelman ............ | A61M 5/172 604/187 |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0206057 A1* | 9/2006 | DeRuntz ........... | A61M 5/31551 604/224 |
| 2008/0027397 A1* | 1/2008 | DeRuntz ........... | A61M 5/31551 604/220 |
| 2009/0275916 A1 | 11/2009 | Harms et al. | |
| 2010/0106099 A1* | 4/2010 | Christiansen ....... | A61M 5/3129 604/208 |
| 2014/0046266 A1* | 2/2014 | Schneider ............... | A61M 5/24 604/187 |
| 2015/0025475 A1* | 1/2015 | Christiansen ....... | A61M 5/3129 604/211 |
| 2015/0133871 A1* | 5/2015 | Stefanski ................ | A61M 5/20 604/209 |
| 2016/0287802 A1* | 10/2016 | Blancke ........... | A61M 5/31551 |
| 2016/0287803 A1* | 10/2016 | Blancke ........... | A61M 5/31551 |
| 2016/0317749 A1* | 11/2016 | Jugl .................. | A61M 5/31501 |
| 2016/0325049 A1* | 11/2016 | Jugl .................. | A61M 5/31555 |
| 2017/0216532 A1* | 8/2017 | Stefanski ................ | A61M 5/20 |
| 2018/0036492 A1* | 2/2018 | Schader ............. | A61M 5/3202 |

FOREIGN PATENT DOCUMENTS

| | | | | |
|---|---|---|---|---|
| EP | 0498737 A1 * | 8/1992 | ........ | A61M 5/31553 |
| EP | 0498737 A1 | 8/1992 | | |
| EP | 0937471 A2 | 8/1999 | | |
| EP | 0937476 A2 | 8/1999 | | |
| JP | S63-318952 | 12/1988 | | |
| JP | H4-256758 | 9/1992 | | |
| JP | H5-103833 | 4/1993 | | |
| JP | 2004-535255 | 11/2004 | | |
| JP | 2007-502146 | 2/2007 | | |
| WO | 9709080 A1 | 3/1997 | | |
| WO | 9938554 A1 | 8/1999 | | |
| WO | 0110484 A1 | 2/2001 | | |
| WO | WO 03/008023 | 1/2003 | | |
| WO | 2005018721 A1 | 3/2005 | | |
| WO | 2008074897 A1 | 6/2008 | | |
| WO | 2013119132 A1 | 8/2013 | | |
| WO | WO-2013119132 A1 * | 8/2013 | | |

OTHER PUBLICATIONS

International Preliminary Report on Patentability in International Application No. PCT/EP2014/074708, dated May 24, 2016, 11 pages.

* cited by examiner

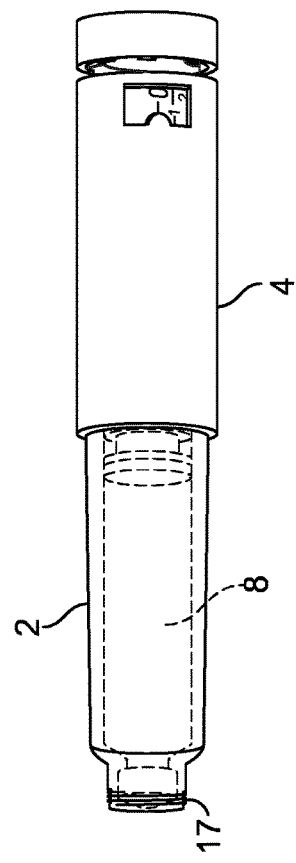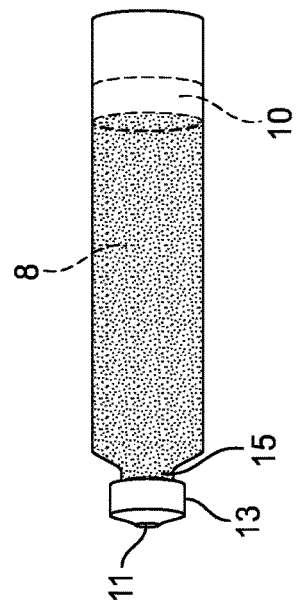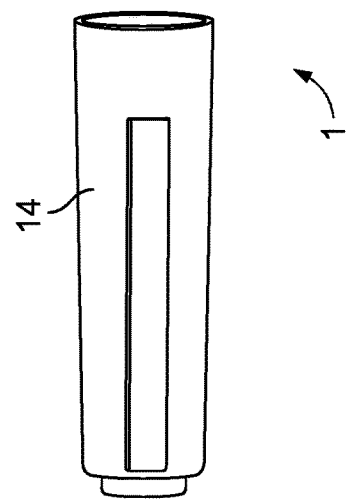
FIG. 1
FIG. 2

ASSEMBLY FOR A DRUG DELIVERY DEVICE

CROSS REFERENCE TO RELATED APPLICATIONS

The present application is a U.S. National Phase Application pursuant to 35 U.S.C. § 371 of International Application No. PCT/EP2014/074708 filed Nov. 17, 2014, which claims priority to U.S. Provisional Patent Application No. 61/907,724 filed Nov. 22, 2013 and European Patent Application No. 14165751.0 filed Apr. 24, 2014. The entire disclosure contents of these applications are herewith incorporated by reference into the present application.

FIELD OF INVENTION

The present patent application is generally directed to an assembly for drug delivery devices, such as pen-type injection devices, and preferably to the dose setting and dose delivery mechanisms for such drug delivery devices. Such devices provide for self-administration of medicinal product from a multi-dose cartridge and permit a user to set the delivery dose. The present application may find application in both disposable and reusable type drug delivery devices. However, aspects of the invention may be equally applicable in other scenarios as well.

BACKGROUND

Drug delivery devices have application where regular injection by persons without formal medical training occurs. This is increasingly common among patients having diabetes where self-treatment enables such patients to conduct effective management of their disease. Diabetes has been shown to cause certain problems. For example, people with diabetes can get high blood pressure, kidney disease, nerve damage, heart disease, and even in certain circumstances blindness. The damage caused by these problems may occur in patients whose blood sugar has been out of control for years. Keeping blood sugar under control, by way of effective insulin administration, is one method that can help prevent this damage from occurring.

In addition, people with diabetes can go into "diabetic coma" if their blood sugar is too high. They can also develop blood sugar that is too low (i.e, hypoglycemia) if they don't get enough food, or they exercise too much without adjusting insulin or food. Both diabetic coma and hypoglycemia can be very serious, and even fatal, if not treated quickly. Closely watching blood sugar, being aware of the early signs and symptoms of blood sugar that is too high or too low, and treating those conditions early can prevent these problems from becoming too serious.

Drug delivery devices have been designed and developed to help patients suffering from diabetes and other disease states so as to prevent such problems from occurring. The circumstances identified above highlight a number of design considerations and criteria for drug delivery devices, especially those that may be used to treat diabetes. As just one example, one requirement is that the drug delivery device must be robust in construction. The drug delivery device must also be easy to use both in terms of the drug delivery device manipulation and understanding of the device's operation. Diabetics, for instance, have to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

Generally, drug delivery devices include a cartridge having a slidable piston and containing a multi-dose quantity of liquid medication. A lead screw extending from the dose setting mechanism of the injector pen is movable in a forward (i.e., distal) direction to advance the piston within the cartridge in such a manner as to dispense the contained medication from an outlet at the opposite cartridge end, typically through a needle that penetrates a stopper or septum at that opposite end. In disposable or prefilled pens, where the cartridge is permanently sealed within the pen housing, after a pen has been utilized to exhaust the supply of medication within the cartridge, the entire pen is then discarded. In reusable pens or devices, after a pen has been utilized to exhaust the supply of medication within the cartridge, the pen is disassembled to allow replacement of the spent cartridge with a fresh cartridge, and then the pen is reassembled for its subsequent use.

A number of drug delivery devices are commercially available and unfortunately a number of those devices suffer from one or more design flaws that may result in the improper use of the injection device or the delivery of an inaccurate dosing of the medicament. Inaccurate dose setting could lead to fatal results. Other design flaws allow the possibility that a counterfeiter can dissemble a disposable pen and insert bogus medicament cartridge. This pen is then reassembled and sold as new. Such design flaws may not be realized when a pen is first commercialized and may only become apparent after the injection device has been in commercial use by patients for an extended period of time. As such, there exists a need to evaluate existing pen designs to identify the design flaws and then take corrective action, which typically would include redesigning certain original mechanisms within the injection device.

A pen injector lending itself to design improvements is described in WO 2005/0188721.

SUMMARY

The present disclosure relates to an assembly for a drug delivery device such as an injector-type device, e.g. a pen-type device.

It is an object of the present disclosure to provide an assembly by which drug delivery devices can be improved. Particularly, by means of the assembly, the device can be embodied in a safer way.

This object is achieved by the subject-matter of the independent claim. Advantageous embodiments and refinements are subject-matter of the dependent claims.

One aspect of the present disclosure relates to an assembly for a drug delivery device. Preferably, the assembly is a resettable drive assembly for the drug delivery device. The assembly comprises a housing and a piston rod having a longitudinal axis, a distal end and a proximal end. Preferably, the longitudinal axis extends through the proximal end and the distal end. The piston rod may, e.g., be a lead screw and comprise a thread. The longitudinal axis of the lead screw may coincide with a longitudinal axis of the housing. The piston rod further comprises a piston rod interaction feature. Said piston rod interaction feature may, e.g., be or comprise a toothing or a row and/or plurality of teeth such as ratchet teeth. The assembly further comprises a piston rod guide being movable with respect to the piston rod, wherein the piston rod further comprises a guide interaction feature corresponding to the piston rod interaction feature, the piston rod guide being movable with respect to the piston rod to switch between a first state and a second state of the assembly, the second state being different from the first state. Accordingly, the guide interaction feature may be a ratchet or coupling arm, for example. The piston rod interaction feature and the guide interaction feature are preferably configured to interact with each other, such as to be coupled or engaged with respect to each other.

In an embodiment, the piston rod guide is displaceably arranged inside the housing. According to this embodiment, the assembly can advantageously be designed such that the guide interaction feature can be selectively brought into or out of engagement with the piston rod interaction feature, for example.

In an embodiment, the piston rod comprises a metal. The piston rod may, for example, be made of a metal. As an advantage, the lead screw may be embodied to be more durable as compared to an embodiment in which the piston rod is made of plastic. Moreover, the piston rod may be more stable as compared to a plastic piston rod.

A further aspect of the present disclosure relates to a drug delivery device comprising the assembly.

Preferably, the piston rod guide serves as a guiding element for the piston rod, e.g. during an operation of the assembly and/or the drug delivery device. Said operation may relate to a dose setting and/or dose delivery or dose dispensing operation. To this effect, the piston rod guide may, preferably, axially guide the piston rod during operation. In the assembly, the piston rod and the piston rod guide are preferably disposed such that the piston rod is axially movable and/or guided through an inside or guiding opening of the piston rod guide.

The assembly is further configured such that, in the first state of the assembly, the piston rod guide is in a first, preferably axial, position relative to the piston rod in which the piston rod interaction feature is arranged to interact with the guide interaction feature to prevent proximal movement of the piston rod with respect to the housing. In this state, the piston rod is, preferably, distally moveable with respect to the housing. The assembly is further configured such that, in the second state of the assembly, the piston rod guide is in a second, preferably axial, position relative to the piston rod, the second, preferably axial, position being different from the first, preferably axial, position, wherein, in the second axial position, the piston rod interaction feature and the guide interaction feature are arranged such that proximal movement of the piston rod with respect to the housing is allowed. The piston rod may, thus, be free to rotate with respect to the housing in the second axial position of the piston rod guide.

The piston rod guide is expediently at least slightly axially moveable or displaceable, e.g. with respect to the housing.

In an embodiment, the assembly is configured such that, in the first state of the assembly, the piston rod is rotationally fixed to the piston rod guide or vice versa and wherein, in the second state of the assembly, the piston rod is either rotationally fixed to the piston rod guide or rotatable with respect to the piston rod guide. In the first state of the assembly, the piston rod guide can advantageously rotationally lock or fix the piston rod which may be crucial for the general function or operation of the assembly and/or the device. The previous embodiment allows to either rotationally fix the piston rod or to enable rotation of the piston rod with respect to the housing when the assembly in the second state. Preferably, the piston rod guide comprises a guide portion or guide feature, such as a guide track by means of or with the aid of which the piston rod can be guided, preferably axially guided. The guide portion, preferably, rotationally fixes the piston rod with the piston rod guide, at least in the first state of the assembly.

In an embodiment, the piston rod interaction feature and the guide interaction feature are designed to form a unidirectional coupling, e.g. an axial unidirectional coupling, between the piston rod and the piston rod guide in the first state of the assembly. Said unidirectional axial coupling is particularly expedient and advantageous for a dispensing operation of the assembly or the device, as, thereby, a distal movement of the piston rod with respect to the housing and/or the piston rod guide may be facilitated while e.g. a proximal movement of the piston rod with respect to the housing and/or the piston rod guide may be prevented. In other words, the assembly may be configured such that relative axial movement of the piston rod with respect to the piston rod guide and/or the housing is—during the usual operation—permitted in the distal direction only. The proximal movement of the piston rod with respect to the housing is, preferably, blocked by the piston rod guide which is, expediently, also not proximally moveable with respect to the housing when the assembly is in the first state.

Said prevention of proximal movement of the piston rod with respect to the piston rod guide and/or the housing addresses an important safety aspect of the assembly and/or the device, as failure or a failure mode of the assembly such as a backward or proximal movement of the piston rod with respect to the housing can—in this way—be prevented. Indeed, by means of a such a backward or proximal movement, a bearing which may be coupled to the piston rod may be lifted off a piston, for example, and thereby an incorrect dose of a drug, such as a dose which is smaller than the one corresponding to the actually set or dialled value (underdose) may be dispensed from the device. This can be prevented by the presented concept as explained in greater detail further below.

In an embodiment, the assembly is configured such that, in the first state of the assembly, a dose setting and/or a dose dispensing can be carried out, and in the second state of the assembly, a resetting operation can be carried out. Said resetting operation, preferably, relates to a proximal movement of a piston rod with respect to the piston rod guide in order to reset the piston rod which may be necessary during a cartridge change, for example.

In an embodiment, the assembly comprises a reservoir, wherein the assembly is configured such that the reservoir can be releasably coupled to the remainder of the assembly and, in the first state of the assembly, the reservoir is coupled to the remainder of the assembly and, in a second state, the reservoir is decoupled from the remainder of the assembly and the piston rod is resettable or movable, preferably towards a proximal initial position.

In an embodiment, the reservoir comprises a cartridge and/or a cartridge holder.

In an embodiment, the assembly is configured such that during decoupling of the reservoir from the remainder of the assembly, the assembly is switched from the first state to the second state.

In an embodiment, the assembly is configured such that the piston rod can be reset by decoupling the reservoir from the assembly and manually or automatically moving the piston rod proximally within the assembly, back to an initial starting position. Said initial starting position, preferably, relates to a position of the piston rod in which a dose has not yet been dispensed from the assembly and/or the device. Said starting position may relate to a proximal-most position of the piston rod with respect to the housing, for example.

In an embodiment, the assembly is configured such that, in the first state of the assembly, the guide interaction feature is in a first radial position with respect to the piston rod, and wherein in the second state of the assembly, the guide interaction feature is in a second radial position with respect to the piston rod, the second radial position being further away from the piston rod than the first radial position.

In an embodiment, the piston rod interaction feature comprises or exhibits a plurality or row of ratchet teeth and the guide interaction feature comprises a ratchet arm. According to this embodiment, in the first state of the assembly, the ratchet arm is preferably engaged, interacts with or abuts the ratchet teeth of the piston rod interaction feature, while, in the second state of the assembly, the piston rod interaction feature is expediently arranged spaced away from the guide interaction feature such that the piston rod interaction feature and the guide interaction feature do preferably not interact.

In an embodiment, the ratchet teeth and the ratchet arm are configured such that a radial movement or displacement of the guide interaction feature with respect to the piston rod interaction feature allows for an expedient and reliable disengagement of the piston rod interaction feature and the guide interaction feature. According to this embodiment, the ratchet teeth, preferably comprise adjacent ramp or slope faces with different inclinations, e.g. with respect to the longitudinal axis. Additionally or alternatively, each tooth may comprise a larger ramp surface and a smaller ramp surface, wherein the larger ramp surface may be stronger inclined e.g. with respect to the longitudinal axis than the smaller ramp surface, for example. In the first state of the assembly, the guide interaction feature preferably abuts said smaller ramp surface of the respective ratchet tooth.

In an embodiment, the piston rod extends through a guiding opening of the piston rod guide, wherein the assembly is further configured such that, in the second state of the assembly, the guiding opening of the piston rod guide is radially enlarged as compared to the first state of the assembly. Said radial enlargement of the guiding opening may be facilitated or achieved by means of a flexible or resilient embodiment of parts of the piston rod guide. This, advantageously, allows for an expedient design of the guide interaction feature, wherein preferably a selective and/or releasable interaction of the piston rod interaction feature and the guide interaction feature can be established.

In an embodiment, the assembly comprises a spring element, wherein, in the first state of the assembly, the spring element tends to move the piston rod guide from the first position to the second position. Preferably, said spring element also tends to move the piston rod guide from the first to the second position when the assembly is switched or being switched from the first state to the second state. By means of the spring element, the mentioned interaction of the piston rod interaction feature and the guide interaction feature can advantageously be embodied releasable or selective in an expedient way.

In an embodiment, the spring element is an integral part of the piston rod guide, wherein the assembly is configured such that, in the first state of the assembly, the spring element tends to move the guide interaction feature from the first radial position to the second radial position. Also, the spring element may tend to move the piston rod guide distally with respect to the housing.

Preferably, the spring element is biased in the first state of the assembly and, in the second state of the assembly the spring element is relaxed as compared to the first state. Advantageously, spring energy, e.g. of the biased spring element, may be used to move the guide interaction feature from the first radial position to the second radial position.

In an embodiment, the piston rod guide comprises a first part and a second part, wherein said parts are connected with each other via a flexible resilient spring part which forms the spring element, wherein the assembly is configured such that, during a switch from the first axial position to the second axial position of the piston rod guide, radial movement of the first and the second part is converted into an axial movement of the piston rod guide. Preferably, the first part, the second part and the flexible resilient spring part form or exhibit a unitary part or component. According to this embodiment, the coupling and/or interaction of the piston rod interaction feature and the guide interaction feature may be embodied advantageously. Further, the assembly may comprise an additional spring or spring element as mentioned above, according to this embodiment.

In an embodiment, the piston rod guide, preferably each of said first and second part, comprises an abutment surface and a further component, such as a housing component of the assembly or another component further comprises a counter surface, wherein the assembly is configured such that the abutment surface abuts the counter surface of e.g. the further component and, when the assembly is switched from the first state to the second state, the abutment surface and the counter surface slide over each other driven by the resilient or spring force of the spring element, thereby displacing or moving the guide interaction feature from the first to the second radial position.

In an embodiment, the piston rod guide is elastically deformable and the spring element is a part separate from the piston rod guide, wherein in the first axial position of the piston rod guide, the piston rod guide is elastically deformed, and in the second axial position of the piston rod guide, the piston rod guide is relaxed or less deformed, at least as compared to the first axial position. According to this embodiment, the mentioned first and second part may be deflectable, preferably resiliently deflectable or displaceable. According to this embodiment, the mentioned first and second part of the piston rod guide are, preferably, elastically deformed and/or displaced. According to this embodiment, the spring element preferably further tends to move the piston rod guide distally only, e.g. from the first axial to the second axial position. When, during the switch from the first state to the second state, the piston rod guide is moved distally, and preferably not radially, also a movement of the guide interaction feature from the first radial to the second radial position may be facilitated. In this way, the piston rod guide may not comprise the above-mentioned flexible resilient spring part but may be formed of an, e.g. intrinsically, elastically deformable material.

In an embodiment, the assembly further comprises a clutch mechanism, wherein the assembly is configured such that, in the first state of the assembly, the clutch mechanism is engaged and rotationally fixes the piston rod guide relative to the housing, and, in the second state of the assembly, the clutch mechanism is released and the piston rod guide is rotatable relative to the housing. By means of the clutch mechanism, the piston rod guide and/or the piston rod may advantageously be rotationally fixed with respect to the housing of the assembly, for example. Said coupling may also be embodied releasable, in this way.

In an embodiment, the piston rod guide comprises a guide portion rotationally locking the piston rod in the first state of the assembly, wherein the assembly is configured such that, in the second state of the assembly, the piston rod guide is (still) rotationally fixed relative to the housing, wherein the guide portion of the piston rod guide is radially arranged such that the piston rod is free to rotate with respect to the housing. According to this embodiment, the guide portion is expediently released from the piston rod. Through the guide portion, as mentioned above, the piston rod may be axially guided. Alternatively, the assembly may be embodied such that the piston rod guide is rotatable relative to the housing, while the guide portion is released from the piston rod.

In an embodiment, the clutch mechanism comprises a clutch spring, a clutch member being axially movable with respect to the housing and the further component, wherein either the clutch member or the further component contacts the piston rod guide in order to engage the clutch or the clutch mechanism. The further component may, according to this embodiment as well be a housing component as mentioned above. Preferably, the further component is rigidly fixed to or integrally formed with the housing. The clutch member may further be axially fixed to the lead screw guide. Furthermore, the clutch member is preferably axially and/or rotationally fixed with respect to the further component and/or the housing.

In an embodiment, the piston rod comprises a thread. According to this embodiment, the piston rod may be embodied as a lead screw threadedly interacting or engaging further components of the assembly for example which may be important to the functioning of the assembly or the device.

In an embodiment, the assembly comprises a drive nut being threadedly engaged and screwable along the thread of the piston rod.

In an embodiment, the assembly comprises an indication member being threadedly engaged with the housing to be screwable relative to the housing. By means of the indication member, advantageously, a dosing state can be indicated to the user.

In an embodiment, the assembly comprises a dose member connected with the drive nut and being axially movable and rotatably or rotationally fixed relative to the drive nut. The dose member is, preferably, rotatably or rotationally fixed with the indication member when the dose member and the indication member are in a first axial arrangement. Moreover, the indication member is, preferably, rotatably relative to the dose member, when the dose member and the indication member are in a second axial arrangement being different from the first axial arrangement.

In an embodiment, the assembly further comprises an inner sleeve being threadedly engaged with the indication member, wherein the inner sleeve is axially movable and rotatably or rotationally fixed relative to the housing. According to this embodiment, the assembly can advantageously be embodied as a drive assembly, e.g. a resettable drive assembly for the drug delivery device.

The following describes a number of design flaws and presents corrective solutions to eliminate these flaws. Additional aspects or information is further given in the following, wherein the set forth aspects are to be interpreted optionally and not necessarily to be essential for the present disclosure.

In most, if not all, devices dose accuracy is significantly affected if the distal end of the lead screw, through the associated bearing, is not in continuous engagement with the proximal end or face of the cartridge piston prior to the user setting a dose. Stated another way, in some dosing mechanism designs there is one or more flaws that allows the lead screw to move or otherwise translate off the piston proximally after a dose is injected and before a subsequent dose is set. In these cases the bearing is no longer in contact with the proximal end of the piston thus creating a gap or void space between the distal face of the bearing and the proximal face of the piston. When a next dose is set and delivered, the lead screw would necessarily traverse this unintended gap before contacting and moving the piston. Because there is no movement of the piston during this gap closure, and hence no expulsion of medicament from the cartridge, the actual dose delivered will be less than that set by an amount directly proportional to the size of the gap. Accordingly, it is of prime importance to prevent any unintended proximal movement of the lead screw between dose delivery and the setting of the next dose. Stated differently, the dosing mechanism must include structures to prevent any proximal movement of the lead screw relative to the cartridge piston.

A physical examination of the re-usable commercial pen injection device that is generally described in WO 2005/018721 shows that if a user pushes the dose knob in the distal direction and simultaneously rotates the dose knob in either direction (clockwise or counter clockwise) a metal lead screw is advanced in either the proximal and distal directions. For example, such a situation can develop as follows. The user begins to set a dose by rotating the dose knob causing the number sleeve to translate out proximally from the body of the injection device. Then, the user grips the number sleeve thereby preventing the number sleeve from rotating and the user also continues to rotate the dose knob while at the same time pushes the dose knob axially in the distal direction—towards the injection site. This causes the clutch to disengage from the dial link thereby allowing relative rotation. Because the existing pen injection device is configured with the dose knob permanently attached to the dial link, rotation of the dose knob necessarily rotates the dial link. Since the dial link is rotationally engaged with the drive nut through the extending fingers, the drive nut also rotates. Rotation of the drive nut while preventing the number sleeve, and hence the inner sleeve, from moving will cause the drive nut to rotate in a fixed axial position. Since the drive nut is prevented from translating or screwing up/down along the lead screw, the lead screw, which is rotational fixed by the mid-body, will be forced to translate axially relative to the threaded connection with the drive nut in either the distal or the proximal direction depending on which way the user turns the dose knob. If the lead screw translates distally, is it possible to push the cartridge piston distally causing unwanted expulsion of medicament from the cartridge. Alternatively, if the lead screw is caused to translate proximally, this proximal movement will cause the lead screw bearing to disengage from the proximal face of the piston creating an undesired gap that will lead to an inaccurate dose. To solve this problem, the present invention modifies the original design of dosing mechanism to prohibit this proximal motion of the lead screw.

The pen type delivery device drug including the above described design improvement includes a housing, a lead screw having a threaded shaft is rotatably or rotationally fixed during dose setting and injecting such that it only moves axially in a distal direction relative to the housing during dose administration and is always prevented from moving proximally. The device also has a fluid container or cartridge defining a medicine-filled reservoir with a movable piston at one end and an outlet at the other end, where the piston is engaged by a bearing connected to the distal end of the lead screw. The piston is advanced toward the outlet or distal end of the cartridge when the lead screw is moved distally during dose administration.

A drive nut is threadedly engaged with the threads on the lead screw and can rotate and move proximally relative to the lead screw and housing during dose setting. A number sleeve is threadedly engaged with the housing and is screwed outwardly in the proximal direction relative to the housing during dose setting. A dial link is slidably and rotationally engaged with the drive nut and is axially movable and rotatably or rotationally fixed relative to the drive nut. The dial link is rotatably or rotationally fixed with the number sleeve through a clutch when the dial link and number sleeve are in a first axial arrangement and when in a second axial position the clutch, and hence the number sleeve, are disengaged from the dial link, the dial link becomes rotatable relative to the number sleeve. An inner sleeve is threadedly engaged with the number sleeve, wherein the inner sleeve is axially movable but rotatably or rotationally fixed relative to the housing. During dose setting, the dial link and the number sleeve are in the first axial arrangement, whereby a screwing motion of the dose knob that is connected to the dial link and number sleeve relative to the housing screws the dial link and the number sleeve a first axial distance from a home position causing the number sleeve to extend in the proximal direction outwardly from the housing or body of the device. The screwing motion of the dial link screws the drive nut along the lead screw threaded shaft a second axial distance different than the first axial distance.

During dose dispensing, the dial link and the number sleeve element are in the second axial arrangement, whereby a screwing motion of the number sleeve relative to the housing back or inward toward the home position advances the inner sleeve without rotation in the distal direction to axially advance the drive nut, and thereby the lead screw and the fluid container piston to dispense medicine from the outlet. The pen injector disclosed herein can be provided with a mechanical advantage that makes it easier for the user to push the dose knob during the dispensing of medication, which mechanical advantage can be very high and conveniently selected by the manufacturer during apparatus designing. This mechanical advantage allows the number sleeve to travel a greater axial distance than the lead screw advances, thus allowing for small doses to be delivered.

The present disclosure may further relate to the following aspects:

1. A drug delivery device comprising:
a cartridge holder configured to contain a cartridge;
a dose setting mechanism coupled to the cartridge holder, the dose setting mechanism comprising:
a housing; a lead screw having a longitudinal axis, a distal end and a proximal end that is rotatably fixed during dose setting and dose delivery and axially movable in a distal direction relative to the housing, the lead screw comprising a threaded shaft and a bearing foot connected to the distal end, the lead screw further comprising a plurality of ratchet arm engaging teeth and a smooth keyway positioned parallel to the longitudinal axis; a lead screw guide axially fixed inside of the housing and operatively coupled to the smooth keyway of the lead screw, the lead screw guide further comprising at least one ratchet arm configured for releasable engagement with the plurality of ratchet arm engaging teeth of the lead screw, so as to prevent undesired movement of the lead screw within the housing.

2. The drug delivery device of aspect 1 further comprising a cartridge contained within the cartridge holder,
wherein the dose setting mechanism is operable to set a dose of a medicament contained within the cartridge.

3. The drug delivery device of aspect 1, wherein the cartridge holder is removably couple to the dose setting mechanism.

4. The drug delivery device of aspect 1, wherein
the lead screw guide further comprises a cone shaped ramp surface,
wherein when the cartridge holder containing a cartridge is coupled to the dose setting mechanism, the cone shaped ramp surface of the lead screw slides along a corresponding ramp surface of the housing so as to compress the lead screw guide and thereby prevent relative rotation of the lead screw guide.

5. The drug delivery device of aspect 1 further comprising
an axially movable clutch operatively configured for engagement with the lead screw guide,
wherein when the cartridge holder containing a cartridge is coupled to the dose setting mechanism, the clutch engages the lead screw guide so as to prevent relative rotation of the lead screw guide.

6. The drug delivery device of aspect 1 wherein the lead screw of the dose setting mechanism comprises a metal lead screw.

7. The drug delivery device of aspect 1, wherein
the lead screw of the dose setting mechanism can be reset by decoupling the cartridge holder from the dose setting mechanism, and manually moving the lead screw proximally within the dose setting mechanism, back to a starting proximal position.

8. The drug delivery device of aspect 1, wherein the lead screw of the dose setting mechanism can be reset by decoupling the cartridge holder from the dose setting mechanism,
and automatically moving the lead screw proximally within the dose setting mechanism back to a starting proximal position.

9. The drug delivery device of aspect 1, further comprising:
a drive nut threadedly engaged and screwable along the lead screw threaded shaft;
a number sleeve threadedly engaged with the housing to be screwable relative to the housing;
a dial link connected with the drive nut and axially movable and rotatably fixed relative to the drive nut, the dial link rotatably fixed with number sleeve when the dial link and number sleeve are in a first axial arrangement, the number sleeve rotatable relative to the dial link when the dial link and number sleeve are in a second axial arrangement; and an inner sleeve threadedly engaged with the number, the inner sleeve axially movable and rotatably fixed relative to the housing.

10. A dose setting mechanism for an injection apparatus, the dose setting mechanism comprising:
a housing;
a lead screw having a longitudinal axis, a distal end and a proximal end that is rotatably fixed during dose setting and dose delivery and axially movable in a distal direction relative to the housing, the lead screw comprising a threaded shaft and a bearing foot connected to the distal end, the lead screw further comprising a plurality of ratchet arm engaging teeth and
a smooth keyway positioned parallel to the longitudinal axis; a lead screw guide axially fixed inside of the housing and operatively coupled to the smooth keyway of the lead screw, the lead screw guide further comprising at least one ratchet arm (232) configured for releasable engagement with the plurality of ratchet arm engaging teeth of the lead screw, so as to prevent undesired movement of the lead screw within the housing.

11. The dose setting mechanism of aspect 10, wherein the lead screw guide further comprises a cone shaped ramp surface, wherein when a cartridge holder containing a cartridge is coupled to the dose setting mechanism, the cone shaped ramp surface of the lead screw slides along a corresponding ramp surface of the housing so as to compress the lead screw guide and thereby prevent relative rotation of the lead screw guide.

12. The dose setting mechanism of aspect 10 further comprising an axially movable clutch operatively configured for engagement with the lead screw guide, wherein when a cartridge holder containing a cartridge is coupled to the dose setting mechanism, the clutch engages the lead screw guide so as to prevent relative rotation of the lead screw guide.

13. The dose setting mechanism of aspect 10 wherein the lead screw comprises a metal lead screw.

14. The dose setting mechanism of aspect 10 wherein the lead screw of the dose setting mechanism can be reset by decoupling the cartridge holder from the dose setting mechanism, and manually moving the lead screw proximally within the dose setting mechanism, back to an original or starting proximal position.

15. The dose setting mechanism of aspect 10 wherein the lead screw of the dose setting mechanism can be reset by decoupling the cartridge holder from the dose setting mechanism, and automatically moving the lead screw proximally within the dose setting mechanism, back to an original or starting proximal position.

These as well as other advantages of the various aspects of our improved assembly and/or drug delivery device, and the manner of attaining them, will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 is an illustration of one embodiment of the present invention showing an assembly or an assembled pen type medication dispensing apparatus or device, where the cap has been removed to reveal the cartridge container affixed to the dose setting mechanism;

FIG. 2 is close up view of the cartridge container and the pen needle that is attached to the cartridge container for injection of the medicament;

Figure 3:
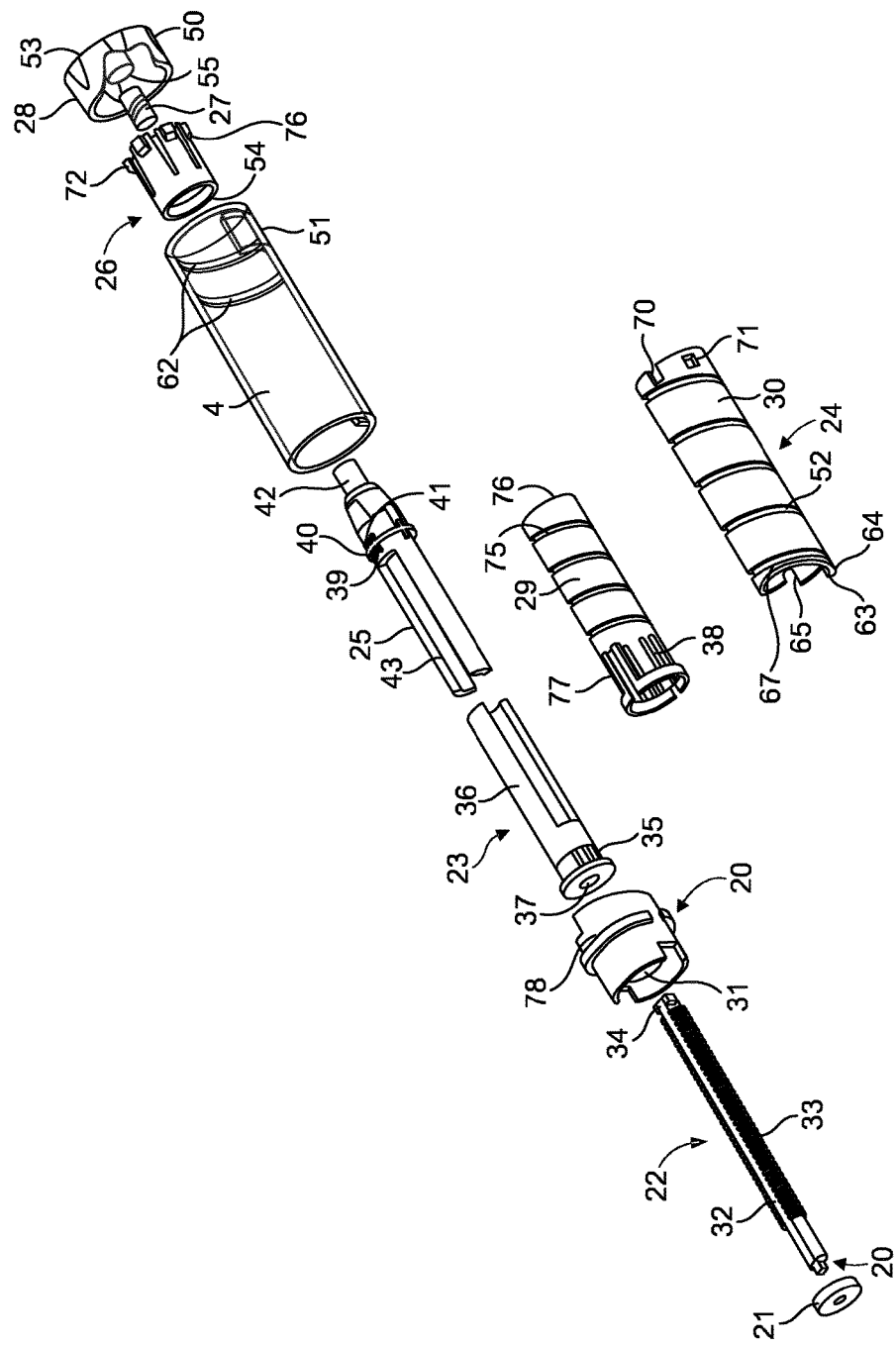
FIG. 3 is an exploded view of the embodiment from FIG. 1 showing each of the individual parts arranged relative to each other as they exist in the fully assembled device.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

Referring first to FIGS. 1 to 3, there is shown a drug delivery device 1 as an injector pen, which pen has an elongated, substantially writing instrument-like form, although other forms are within the scope of the invention. In other words, the drug delivery device may be a pen-type device. The drug delivery device 1 comprises a housing having a cartridge holder 2, and main (exterior) body or housing 4.

The numeral 113 indicates an assembly, wherein the parts or components of the assembly are preferably comprised or relate to the device 1. Reference to the assembly may actually also relate to the injector or the device. Preferably, the assembly 113 is a resettable drive assembly for the drug delivery device 1.

The drug delivery device 1 and the housing have a distal end and a proximal end. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis or rotational axis of the device 1.

The proximal end of the cartridge holder 2 and the distal end of the main housing 4 are secured together by appropriate retaining features depending on whether the pen injector is designed as a reusable device or as a disposable device. In the latter case, the retaining feature would be permanent using the connection means described below. If the device is reusable, the retaining meaning would be a screw type connection, a Luerlok, snap-fit, bayonet, or the like type or combination of fittings that allow the user to easily disassemble the device to replace the empty cartridge with a fresh new cartridge. In this illustrated arrangement, the cartridge holder 2 is secured within the proximal end of the main body 4.

A cartridge 8 from which a number of doses of a medicinal product may be dispensed is provided in the cartridge holder 2. Preferably, the cartridge contains a type of medicament that must be administered often, such as once or more times a day. One such medicament is insulin. A piston 10 shown in FIG. 2 is initially retained in the proximal end of the cartridge 8 and as each injection is completed gradually moves distally to the empty cartridge position. A removable cap 14 is releasably retained connected to the main body 4 covering the cartridge holder 2.

The dose setting mechanism of the drug delivery device illustrated in FIGS. 1-3 may be utilized as either for a disposable or reusable drug delivery device. Where the drug delivery device comprises a disposable drug delivery device, the cartridge cannot be removed from the device without destroying the device 1. In a disposable device, the proximal end of the cartridge holder 2 can be fixedly mounted or secured, via adhesives, ultrasonic welding or in another suitable manner, to the dose setting mechanism housing when the injector pen is assembled by the manufacturer. Alternatively, where the drug delivery device 1 comprises a reusable drug delivery device, the cartridge 8 is removable and may be removed from the device 1 without destroying the device. In the drug delivery device 1 illustrated in FIGS. 1-3, the device is illustrated as a disposable drug delivery device. However, those of ordinary skill in the art will recognize that the dose setting mechanism could also be used on reusable drug delivery devices as well, while in the case of a reusable pen, wherein the cartridge holder 2 may be reusable, such that the proximal end can be removably mounted or secured, for example via a threaded, bayonet, or snap fit connection, to a reusable dose setting mechanism having a resettable lead screw.

The previously mentioned removable or replaceable cap 14 is used to cover the cartridge holder 2 extending from the main housing 4. Preferably, the outer dimensions of the replaceable cap 14 are similar to or identical to the outer dimensions of the main housing 4 so as to provide an impression of a unitary whole part when the replaceable cap 14 is in position covering the cartridge holder 2. In use, the removable cap 14 is removed and a pen needle 16 assembly comprising a double-ended needle mounted in a hub may be screwed or pushed onto the distal end of the cartridge holder or alternatively may be snapped onto this distal end.

Cartridge 8 is of conventional design and defines a medicine-filled reservoir that is closed at its proximal end by the piston 10 that is axially slidably and sealably engaged with the cartridge interior wall to hold the fluid medication within the reservoir. The distal, outlet end of the cartridge reservoir is sealed by a septum 11 held by a cap 13 that is secured to a stepped-down diameter neck portion 15 of the cartridge 8. When the pen needle assembly 16 is mounted on the distal end of the cartridge holder 2, the proximal point of the injection needle 16 passes through a central opening in the distal end of the cartridge holder 17, an opening in cap 13, and penetrates the cartridge septum 11 to provide a fluid flow outlet by which medicine within the cartridge reservoir can be dispensed from the distal needle tip during operations of injector pen 1. The fluid medicine cartridge shown and described above is illustrative and not intended to be limiting as other constructions may be employed within the scope of this invention. The main body 4 of injector pen 1 houses an axially advanceable lead screw 22, a drive nut 23, an inner sleeve 29, a dial link 25, a number sleeve 24, a clutch 26, and a compression spring 27. A dose knob 28 is connected to the dial link 25 and is used to set the dose and then to inject the set dose. Housing or main body 4 is formed from a lightweight material, such as injection molded plastic. The housing 4 may be molded as a single, tubular piece for robustness. A window 51 in the housing 4 near its proximal end can be filled with a magnifying lens that snaps fits to the housing 4 and allows dosage indicating markings (not shown) on the number sleeve 24 to be readily visible during use.

Near the interior distal end of the housing 4 is mounted a mid-body 20 that is formed with an a central opening having an inward facing anti-rotation mechanism formed from of a pair of diametrically opposed elements or tabs 31 having squared off inward ends that each slidably fit within longitudinal keyways 32 in the lead screw 22. In alternate embodiments, features other than tabs and keyways, for instance a lead screw with flats that fits within a complementarily shaped hole in a collar, may be used to prevent rotation. The tabs 31 prevent the lead screw 22 from rotating within the housing 4 during pen use, but permit the lead screw 22 to be shifted longitudinally, such as in the distal direction towards the cartridge 8. A snap fit or sonic welding connection of the mid-body 20 to the tubular housing 4 can be used to prevent axial and rotational relative motion of the mid-body 20 to the housing.

The lead screw 22 is in the form of a screw that is axially translatable and rotatably fixed during dosing and injecting. The term "rotatably fixed" shall mean in this context that the lead screw 22 is prevented from rotation during dosing and injecting. The lead screw 22 includes a shaft with a helical the threading 33 along its length, which threading 33 is interrupted by the longitudinally extending keyways or grooves 32. A thread stop 34 shown at the proximal end of threading 33 is provided and is used in preventing the pen from being set by a user to deliver a dose of medicine larger than remains in cartridge 8. Other forms of stopping the screw motion may be substituted within the scope of the invention, for example, the threading at the proximal screw end could stop near the proximal end where it cannot be cammed in, and such solid screw with thread stop better ensures the nut 23 will not be torqued off the screw during dose setting. The distal end of lead screw 22 includes an enlarged, disc-shaped foot or bearing 21 to distribute loading on the cartridge piston 10 that the bearing contacts and thereby directly engages during piston advancing. The separate bearing foot can be attached, such as with a snap fit that may permit relative rotation, to the lead screw. The lead screw 22 is shown as being a one-piece plastic injection molding, but alternate materials of construction and multiple pieces are possible.

The drive nut 23 includes a cylindrical, tube-shaped body with flexible fingers 36 and clicker teeth 35. The distal region of the drive nut 23 is formed with an internal threading 37 that threadedly engages in a friction locking fashion the threading 33 on lead screw 22. Threadings 33 and 37 are shown as a double start threading but may be differently formed while still providing suitable friction locking capabilities, such as a single start threading or another multiple start threading. The drive nut 23 is located within inner sleeve 29 and is axially, but not rotationally fixed, to the inner sleeve. As the drive nut 23 is rotated relative to the inner sleeve 29 during dose setting, the clicker teeth 35 engage in a ratchet fashion flexible arms 38 that project radially on the inside of inner the sleeve 29. As the drive nut rotates the flexible arms ride over the teeth 35 creating an audible clicking noise. The teeth 35 are configured so that each click is equal to one dose volume being set. As few as one flexible clicker arm 38 may be provided, but the use of four equally angularly spaced arms aids in centering the drive nut 23 within the inner sleeve 29. The hollow interior of drive nut body 23 located proximally of the threading 37 allows free passage of the proximal end of lead screw 22. The exterior surface of drive nut 23 is designed to cooperatively engage with the dial link 25 so that the dial link 25 is axially free and rotatably fixed relative to drive nut 23. Thus, during use the dial link is axially moveable relative to, but rotatably locked with, the threaded drive nut. This connection is possible because of the cooperation of proximally extending fingers 36 on the drive nut 23 and the distally extending fingers of dial link 25. These two sets of fingers move axially relative to each other but engage each other rotationally during dose setting when the dial link is rotated by turning dose knob 28, which is fixed to the dial link 25. The drive nut 23 is shown as being a one-piece plastic injection molding, but other constructions are within the scope of the invention.

In the shown embodiment, the dial link 25 is formed in one piece of an injection molded plastic and which fits within body 4. A flange 40 that rings a central region of the dial link body includes splines or teeth 39 that extend from the distal face of the flange 40, and teeth 41 that extend from the proximal face of the flange 40. A stepped-down portion of the proximal end of the dial link 25 forms an axially and proximally extending stem 42. The distal end of the dial link body includes a pair of fingers 43 that fit with fingers 36 of the drive nut 23 to allow axial motion but not rotational motion of the drive nut 23 relative to the dial link 25, thereby rotationally locking the pieces together within the same annular space. Fingers 36 and 43 extend sufficiently axially to ensure they do not disengage during the setting of the maximum pen dose for injection.

An injection molded plastic dose knob 28 with a proximal face, and having a distally facing and centrally located bearing collar and alignment post 55 is provided. The stem 42 of the of the dial link 25 receives the dose knob alignment post and can be ultrasonically welded within the bearing collar during manufacturing assembly, so as to axially and rotatably fix together the dose knob 28 and the dial link 25. The term "rotatably fix" shall mean in this context that any relative rotational movement between the dose knob 28 and the dial link 25 is prevented. Dose knob skirt 50 distally extends from the radial periphery of the dose knob distal face to serve as a grip portion for a user during dose setting.

Coaxially mounted around the dial link 25 is number sleeve 24. The number sleeve 24 has a cylindrical exterior surface 30 with a threading 52 formed as a helical groove that engages a corresponding threading 62 formed on the interior surface of body 4 to threadedly engage the number sleeve 24 to the pen housing. Threadings 52 and 62 are shown as a single start threading but may be differently formed. Threading 62 abuts an end 63 of threading 52 on the number sleeve 24 at the maximum pen dose, assuming the cartridge 8 is sufficiently full for such a maximum dose. A stop surface 64 on the distal end of the outer surface of the number sleeve is positioned in slightly spaced apart relationship with a projecting stop at the zero dose position, and another stop surface is to be abutted by the stop if a user attempts to manually screw the screw element below a zero dose position. A hollow interior 65 of the number sleeve 24 is defined by a cylindrical interior surface provided with a helical threading 67.

The outside diameter of the number sleeve 24 is selected such that it can fit inside the dose knob 28. The proximal end region of the number sleeve 24 includes a number of notches 70 and corresponding windows 71 that are alternately spaced around the circumference. The number sleeve 24 includes around its exterior surface 30 suitable indicia of therapeutic dose size as visible through the body opening or window 51. The clutch 26 fits within the open proximal end of the number sleeve 24. Ears 72 on the clutch 26 fit within notches 70 and assembly fingers 73 snap lock into windows 71 to axially and rotatably lock the number sleeve and the clutch 26 together during manufacturing assembly. A ring of axially extending teeth 54 on the clutch 26 formed in the interior surface of flange cooperate with the dial link teeth 41 proximally facing on dial link 25.

Disposed between the clutch 26 and the inside portion of the dose knob 28 is the compression or biasing spring 27 that urges the clutch 26 to engage the teeth 41 on the dial link 25. During injection, when a user manually applies a plunging force onto the proximal face of dose knob 28, the spring 27 is elastically compressed, thus disengaging the clutch 26 and the number sleeve 24 from the dial link 25. The flange teeth 41 on the dial link 25 and the clutch teeth 54 mesh when the spring 27 has biased the clutch 26 and attached number sleeve 24 to the dose knob 28 and dial link 25. The dose knob 28 and the dial link 25 are not meshed with the clutch 26 and number sleeve 24 when the spring 27 has been sufficiently compressed during injecting. While a helically coiled metal wire spring is shown, other forms of commonly known biasing elements may be substituted.

The inner sleeve 29 is injection molded from plastic and includes a tubular body that fits into the hollow 65 of the number sleeve 24. The inner sleeve 29 has a helical threading 75 on its outer surface that engages internal the threading 67 on the inside surface of the number sleeve 24. Threadings 67 and 75 are shown as a single start threading, but may be differently formed. The proximal-most portion of the end of inner sleeve 24, which end is partially helically shaped corresponding to the threading, is notched to form a partial ring of axially projecting teeth 76 that, when meshed with dial link 25 distally facing teeth 39, serve to rotatably lock together the dial link and the inner sleeve. Inner sleeve 29 is keyed to pen body 4 through the intermediate mid-body 20 that is axially and rotationally fixed to the body 4. The distal end of the inner sleeve 29 has a pair of ridge-defined slots 77 on the periphery of the inner sleeve 29 which axially, slidably receive lugs 78 radially inwardly projecting from the mid-body 20.

Openings molded into the inner sleeve 29 define four resilient fingers 38 having radially inwardly projecting teeth that are axially oriented and shaped to project into a recess in the distal end of the drive nut 23 that has radially projecting teeth or ridges 35 such that the inwardly projecting teeth click over, in either rotational direction, teeth 35 during dose setting. Fingers 38 with teeth cooperate with the recess on the drive nut to hinder the nut from coming off the inner sleeve 29 after being assembled thereto during manufacture.

To facilitate back-driving during dose delivery, the threaded connections of the number sleeve 24 and the body 4, and the number sleeve and the inner sleeve, are non-binding and provided by projecting 60° face angle threads that slide within correspondingly designed recessed grooves. With these threadings, it is preferred that the mechanical advantage is 3.4 or greater, and the screw lead of the drive member or drive nut is 0.108 inch.

The operation of the above described embodiment will now be explained. The pen 1 with a needle 16 attached should first be primed to remove any trap air in the cartridge and to ensure the bearing is in contact with the proximal end of the cartridge stopper or piston 10. In particular, typically while clutching the pen body 4 in one hand, a user manually grips dose knob skirt 50 and then begins to turn the knob 28 relative to the body 4. At the zero dose arrangement, and as long as the knob 28 is not also being plunged which is improper, the knob 28 can only be rotated in a dose increasing direction due to the number sleeve not being further movable distally. A user stops the rotating after a short amount of number sleeve travel that is associated with a small delivery volume, such as one or two units, which is indicated by the markings visible through window 51. Then, and after removing cap 14 and any other needle cap present, and while pointing the needle tip upward, the user applies a plunging force on dose knob 28 to drive it distally until the number sleeve returns to the zero dose position, at which the number sleeve threading 52 has reached the distal end of the body threading 62, during which plunging action the piston 10 is shifted forward within the cartridge 8. If a user sees that the piston movement has caused liquid to reach the needle distal tip, the priming process is complete. If no liquid is visible at needle tip, the priming steps are repeated as needed. After priming, the pen 1 is ready to be used for an actual injection.

First, a user prepares the pen by setting the desired dose, as visible in the window 51, by turning of knob 28. If the user dials up too large of a dose, and without expelling any medicine, the user can rotate down the dial by turning the knob 28 in the opposite direction, all the way back to zero if desired. To set a dose, the knob 28 is turned in a clockwise direction. Because the dose knob 28 and the dial link 25 are fixed rotationally, the dial link 25 is rotated causing the distally facing fingers 43 to engage the proximally facing fingers 36 of the drive nut to thereby turn the drive nut 23 in same direction. Rotation of the drive nut causes the nut to rotate relative to the stationary lead screw 22 whereby the nut 23 moves or climbs up the lead in the proximal distance. The drive nut 23 rotates relative to the inner sleeve 29 that is held rotationally fixed relative to the body 4 through the splined connection to the mid-body 20. Because the drive nut 23 and inner sleeve 29 are axially fixed, proximal axial movement of the drive nut 23 causes the inner sleeve 29 to slide proximally relative to the mid-body 20. Because the clutch 26 is rotationally fixed with the dial link 25 the clutch 26 rotates causing the number sleeve 24 to rotate and to spin out proximally away from body 4. Because the pitch of the threads on the number sleeve 24 are greater than the pitch of the threads on the inner sleeve 29, the number sleeve 24 and the dial link 25 will translate a larger axially distance compared to the inner sleeve 29 and the drive nut 23.

To inject the dose, after pen 1 is manipulated so the injection needle distal tip properly penetrates, for example, a user's skin, an axial, distal plunging force is applied to the knob face 53 to force the dial link 25 axially in the distal direction toward the body 4, such as with a thumb or index finger of the hand which grasps the housing 4. Initially during injecting, the dial link 25 is shifted axially, which shifting motion compresses the biasing spring 27 to close the gap between the knob surface and the proximal end of the number sleeve. The biasing spring is designed to compress prior to the number sleeve 24 moving relative to the body 4. When dial link 25 shifts relative to the number sleeve 24 to the axial arrangement of the drive nut 23, the clutch teeth 54 and dial link teeth 42 disengage to allow a back-driving rotation of the number sleeve 24 relative to the dial ink 25. During the axial movement of the dial link 25, drive nut 23 does not move axially or rotationally. When the number sleeve 24 and clutch 26 rotatably uncouples from the dial link 25, as the dial link 25 is continued to be axially plunged without rotation by the user by the plunging of knob 28, the number sleeve 24 screws into the body 4 as it spins relative to knob 28 and the dose markings on the number sleeve 24 that indicate the amount still remaining to be injected is visible through window 51.

As it screws down, number sleeve 24 causes the inner sleeve 29 to in essence screw up the internal thread inside of the number sleeve threading as the inner sleeve advances distally a lesser distance than the number sleeve. The advancement of the inner sleeve, due to the abutting or direct engagement with the distal end of the drive nut 23, advances drive nut 23 without rotation, which due to its threaded connection with the lead screw 22 advances the lead screw 22 axially without rotation, which lead screw advancement shifts cartridge piston 10 to expel medication from the cartridge reservoir. The injection is completed when the number sleeve threading 52 has reached the distal end of the body 4, at which time pen 1 is once again arranged in the ready state or zero dose position.

Pen 1 can continue to be used to deliver any desired dose until the medicine remaining in the cartridge 8 is insufficient for a proper dosing. This insufficiency is indicated to the user by the inability to fully set the desired dose due to drive nut threading 37 abutting thread stop 34 of the lead screw 22, at which time the drive nut 23 and dial link 25 cannot be rotated proximally any farther. When insufficient medicine remains, the pen 1 is to be disposed of and replaced with a similar but entirely new pen.

Figure 4:
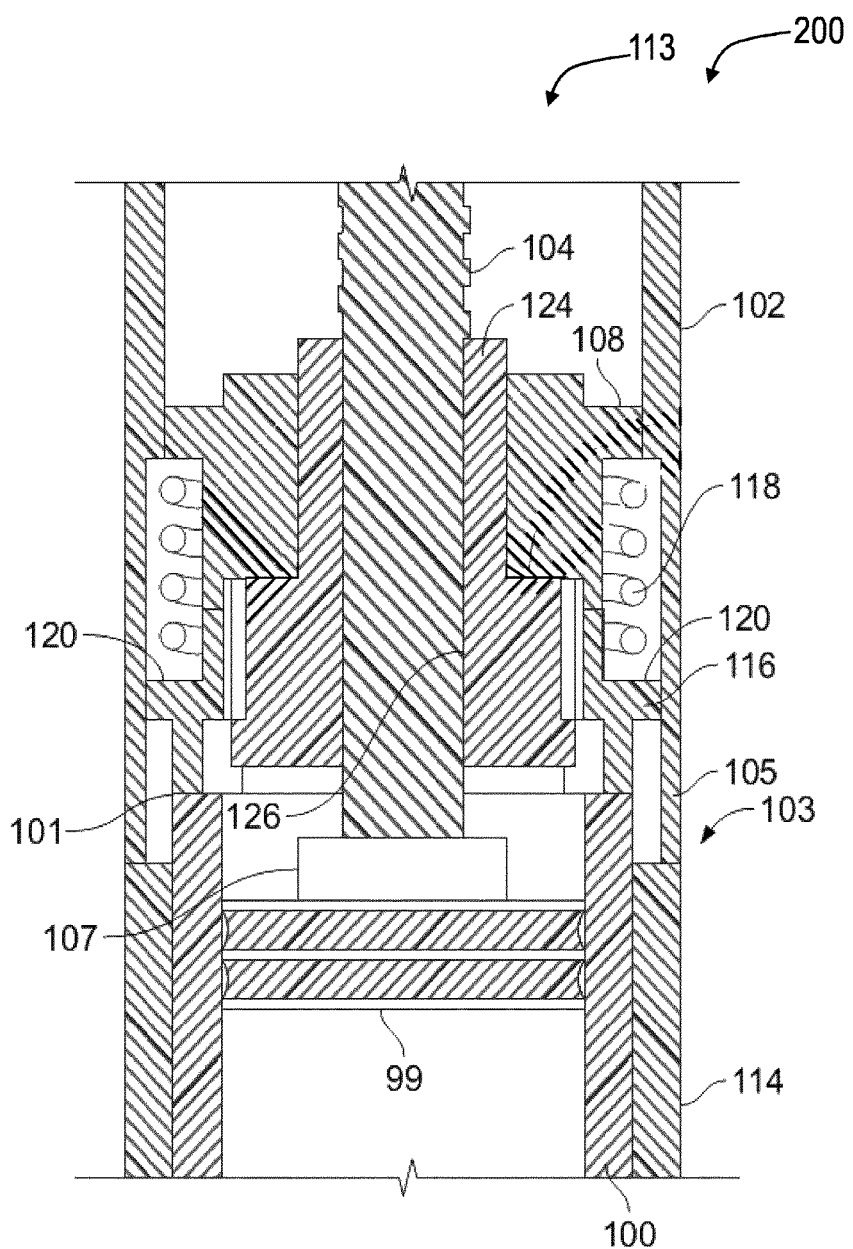
FIG. 4 is a cross-sectional view of a portion of an embodiment of a reusable pen type medication dispensing apparatus with an attached cartridge housing.

FIG. 4 is a cross-sectional view of a portion of an embodiment of a reusable pen type medication dispensing apparatus or device 200 comprising an assembly 113 and/or a dose setting and/or drive mechanism that is attached to the cartridge holder 114. The reusable device 200 is similar in many respects as to how the pen illustrated in FIGS. 1-3 functions to set a dose of medicament and how it functions to then inject this set dose, as discussed in greater detail above. One difference is that the reusable pen apparatus 200 is adapted for use as a reusable pen type apparatus. That is, when the cartridge 100 contained within the cartridge holder 114 of this pen apparatus 200 no longer contains any medication, the cartridge holder 114 can be removed from the dose setting mechanism. The empty cartridge can be removed and discarded and a new, full cartridge can be inserted into the cartridge holder 114. Before the cartridge holder 114 is reconnected to the dose setting mechanism, the lead screw 104 of the pen apparatus 200 must be reset by moving the lead screw back proximally within the dose setting mechanism, back to an original or initial starting or initial proximal position. This lead screw 104 can be reset by a user by pushing the lead screw 104 in the proximal direction, thereby manually pushing the lead screw 104 back to the original or starting position. Alternatively, the lead screw 104 can be automatically reset by the user simply tilting the distal end of the assembly 113 or dose setting mechanism upwards, allowing the weight of the lead screw 104 to automatically return the lead screw to its original or starting position under its own weight.

As illustrated, the reusable pen apparatus 200 comprises a housing or body 102 that houses the dose setting mechanism or assembly: the mechanism that is used to set a user defined dose. At a distal end of this housing 102, a reversible coupling mechanism 103 (such as a thread or a bayonet mechanism) is provided. This reversible coupling mechanism 103 can be adapted to receive a corresponding distal end of the reusable cartridge holder 114. As illustrated, the lead screw 104 comprises a lead screw bearing 107 that is illustrated as residing along a stopper 99 of the cartridge 100. Preferably, the lead screw 104 comprises a metal lead screw.

As can also be seen from FIG. 4, the assembly 113 or the dose setting mechanism further comprises a clutch 116, a cartridge spring 118, and a lead screw guide 124. The clutch 116 and the lead screw guide 124 are clipped together so that they move axially together but cannot move axially relative to one another. Moreover, the clutch 116 is rotationally keyed to an inner portion or an inner surface 105 of the mid-body 20 (see in FIG. 3), which may—in FIG. 4—relate to the housing shoulder 108 or a further component of the housing for example, and is therefore prevented from rotating. When the cartridge holder is operatively attached to the dose setting mechanism, a distal end 101 of the cartridge 100 pushes upon the non-rotatable clutch 116 so that the clutch 116 will be biased in a distal direction by way of a cartridge spring 118. This cartridge spring 118 is configured to reside near an annular face of the clutch shoulder 120 and a distal face of a housing shoulder 108. In the illustrated position of FIG. 4, when engaged by the distal end of the cartridge, the clutch 116 cannot rotate with respect to the body 102.

A lead screw guide 124 is operatively coupled between the lead screw 104 and a proximal portion of the clutch 116. The lead screw guide 124 comprises a plurality of teeth provided along a proximal lead screw guide surface. These teeth are configured to engage or couple complementary teeth on a distal end of the housing shoulder 108 (teeth not explicitly indicated). Therefore, in the position illustrated in FIG. 4 where these teeth reside in meshed engagement, the lead screw guide 124 is not rotatable. However, when the cartridge housing 114 is decoupled from the dose setting mechanism, the lead screw guide 124 can move into a rotatable position. That is, when the cartridge housing 114 is decoupled from the remainder of the assembly, the lead screw guide 124 and the clutch 116 move together axially relative to the housing, so that the teeth between the lead screw guide 124 and the housing shoulder 108 disengage and the lead screw guide 124 can be reset by rotation relative to the clutch 116. Although not being explicitly indicated, the assembly can be configured such that, e.g. in a cross sectional view, the housing shoulder or the part comprising the same at least partly surrounds the clutch.

Alternatively, the assembly can be configured such that the above described clutch mechanism can be established between the lead screw guide and the clutch, wherein these parts may then expediently comprise the corresponding clutch or engaging teeth.

In addition, lead screw guide 124 comprises a pair of guide members or portions 126 that are configured to engage and slide within the longitudinal grooves of lead screw 104. This configuration allows the lead screw 104 to be rotatably or rotationally fixed with respect to the body 102 but being allowed to move either distally or proximally relative to the lead screw guide 124, such as during a dose setting step, a dose injecting step and/or a device resetting step.

Figure 5:
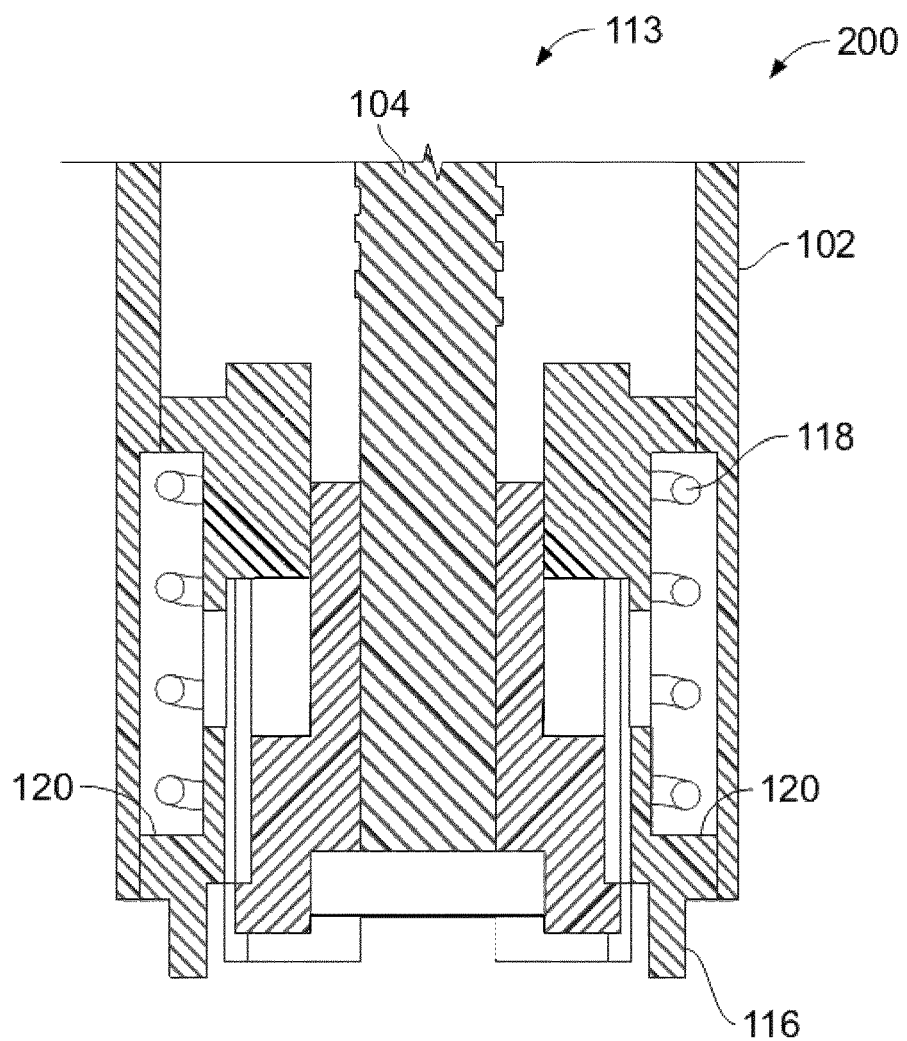
FIG. 5 is a cross-sectional view of the embodiment illustrated in FIG. 4 with the cartridge housing removed from the reusable pen type medication dispensing apparatus.

When all of the medicament contained within the cartridge 100 has been expended, the cartridge may be removed from the cartridge holder 114 by uncoupling the cartridge holder from the assembly 113 or the dose setting mechanism. For example, FIG. 5 is a cross-sectional view of the embodiment illustrated in FIG. 4 with the cartridge holder 114 removed from the reusable pen type medication dispensing apparatus 200. As illustrated, once the cartridge holder 114 has been uncoupled, this releases the cartridge spring 118 which then can drive the clutch 116 along with the lead screw guide 124 in a distal direction since these two components remain clipped together. The clutch 116 and the lead screw guide 124 then travel to a distal end position as shown in FIG. 5. At this distal end position, the clutch 116 is axially retained in the end position within the housing 102. The lead screw guide teeth are, e.g. moved out of engagement with the corresponding housing shoulder teeth. Consequently, lead screw guide 124 is now free to rotate along the lead screw 104 and relative to the body 102. Therefore, during a dose setting mechanism reset step, the lead screw 104 may now be pressed in the proximal direction, and thereby screwed into the previously described drive nut, to a starting position for use with the next cartridge.

As described above, physical examination of the commercially available reusable pen injection device that is generally described in WO 2005/018721 and represented part in by the apparatus 200 illustrated in FIGS. 4 and 5, shows that if a user pushes the dose knob in the distal direction and simultaneously rotates the dose knob in either direction (clockwise or counter clockwise) the lead screw can be advanced in either the proximal and distal directions since the lead screw 104 is not prevented from moving axially vis-à-vis the lead screw guide 124. To solve this problem, the present invention modifies the original design of dosing mechanism as described above with reference to FIGS. 4 and 5 to prohibit this proximal motion of the lead screw.

Figure 6:
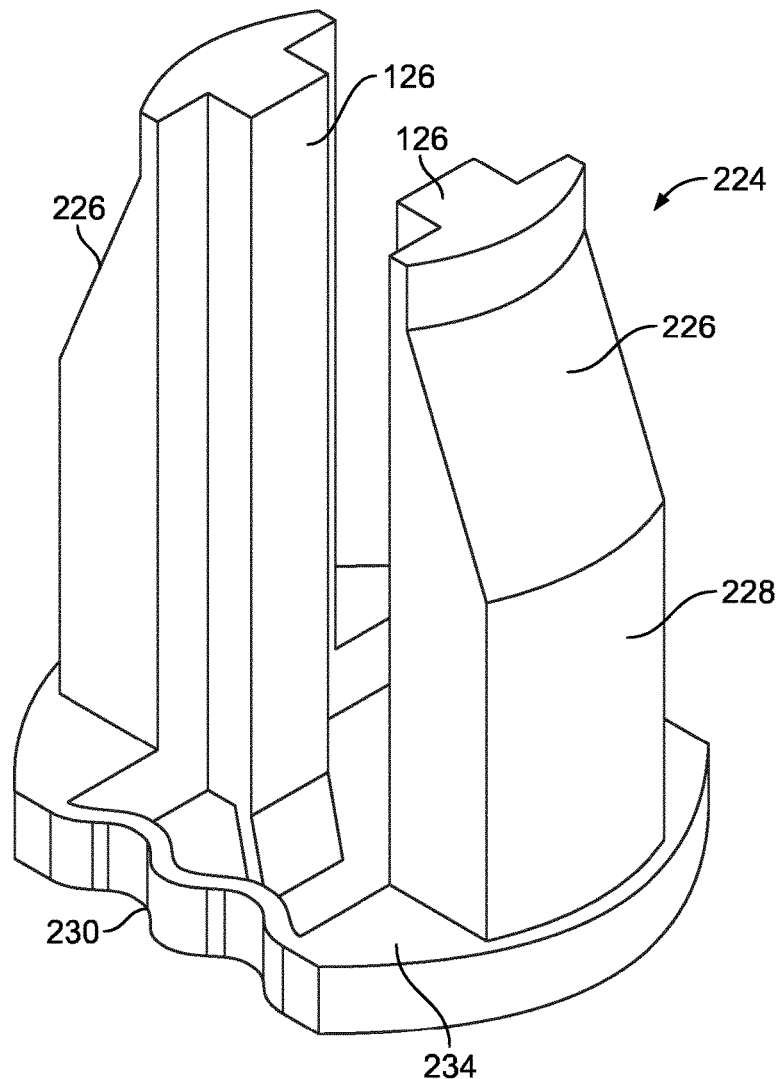
FIG. 6 is a perspective view of a modified lead screw guide that can e.g. be used in the pen type medication dispensing apparatus illustrated in FIGS. 4 and 5.

For example, FIG. 6 illustrates a modified lead screw guide 224 that may be used with the reusable pen injection device illustrated in FIGS. 4 and 5 and generally described above. As illustrated, this modified lead screw guide 224 comprises a lead screw guide main body 228 and this main body 228 comprises a bottom ledge 234. Two cone shaped ramps 226 extend away from this bottom ledge 234. These cone shaped ramps 226 also comprise a pair of guide members 126. In addition, the modified lead screw guide 224 further comprises a pair of ratchet arms 232 configured along a bottom surface of the bottom ledge 234. These ratchet pair arms 232 can be seen from FIGS. 7A and 7B. The modified lead screw guide 224 further comprises a biasing member 230 which allows the modified lead screw guide 224 to exhibit a certain degree of compressibility, flexibility or resiliency as will be explained below.

Figure 7A:
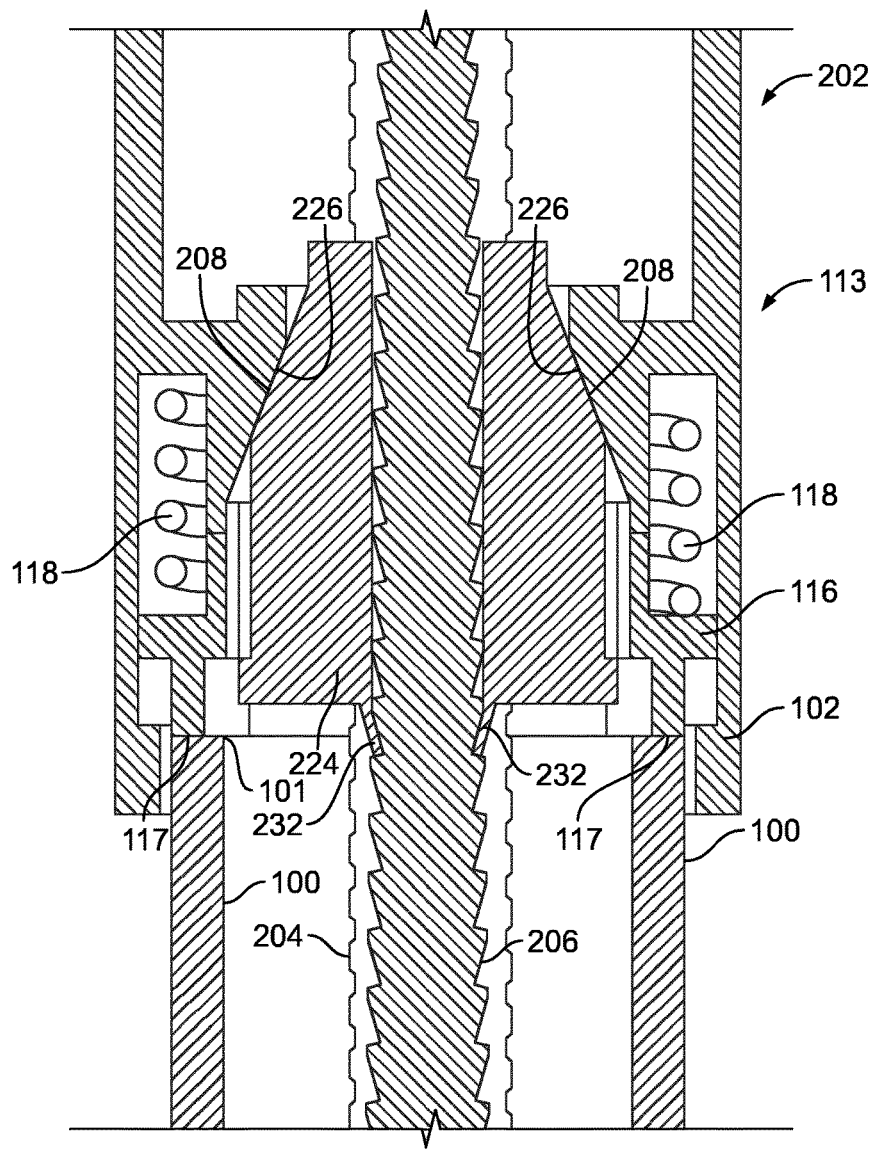
FIG. 7A is a cross-sectional view of a portion of an alternative reusable pen type medication dispensing apparatus utilizing the modified lead screw guide of FIG. 6 with an attached cartridge housing.
Figure 7B:
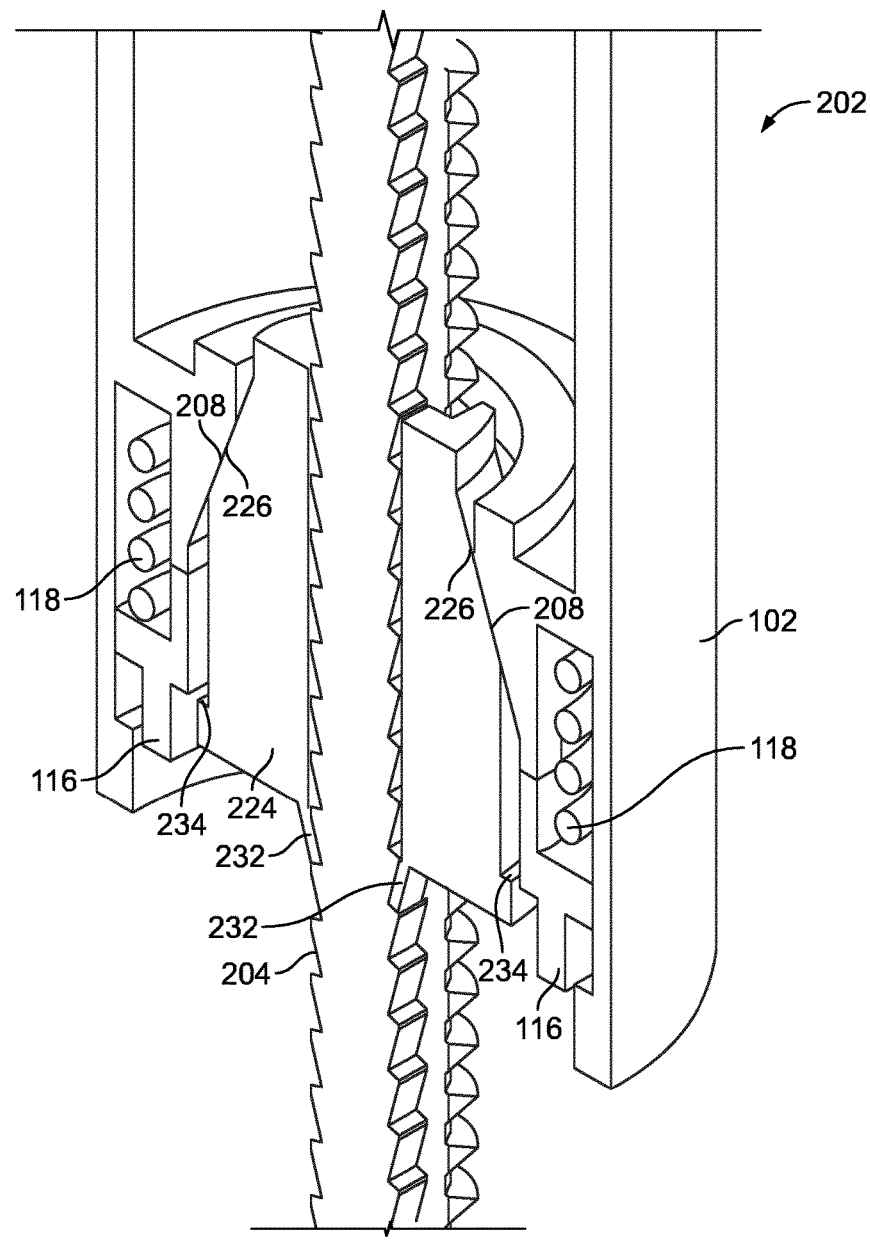
FIG. 7B is an alternative cross-sectional view of a portion of the alternative reusable pen type medication dispensing apparatus or device illustrated in FIG. 7A.

For example, FIG. 7A illustrates the reusable pen type injection apparatus 202 illustrated in FIGS. 4 and 5 further comprising the modified lead screw guide 224 illustrated in FIG. 6. FIG. 7B illustrates this modified injection apparatus 202 in yet an alternative perspective view. Aside from utilizing a modified lead screw guide 224, this modified reusable pen type injection apparatus 202 further comprises a modified lead screw 204 and a modified housing shoulder 208. For example, the modified lead screw 204 has been modified to comprise a set of ratchet arm engaging teeth 206 configured so as to engage the modified lead screw guide ratchet arms 232 when the lead screw guide 224 has been compressed into a seated position, as illustrated in FIG. 7A.

In FIGS. 7A and 7B, the cartridge 100 has been included or mounted but the cartridge holder has been omitted for ease of discussion. As illustrated, when the cartridge holder is coupled to the assembly 113 or the dose setting mechanism, a distal end 101 of the cartridge 100 acts on an engaging surface 117 of the clutch 116. In this mounted position, the cartridge holder pushes in the proximal direction against the clutch 116. As the clutch 116 moves in the proximal direction, the cone-like slanted portions of the lead screw guide push the modified lead screw guide 224 into its proximal end position, as illustrated in FIGS. 7A and B. As shown, the lead screw guide cone shaped ramps 226 push along a modified housing shoulder 208 that is also ramped. Therefore, as the lead screw guide 224 continues to be pushed in the proximal direction, the lead screw guide will become compressed and the ratchet arms will be squeezed into the ratchet arm receiving teeth of the modified lead screw 204. With such a modified lead screw guide configuration, if a user pushes the dose knob in the distal direction and simultaneously rotates the dose knob in either direction (clockwise or counter clockwise), the interaction between the lead screw guide ratchet arms 232 and the lead screw ratchet arm engaging teeth 206 prevent the lead screw 204 from advancing in the proximal direction.

Figure 8:
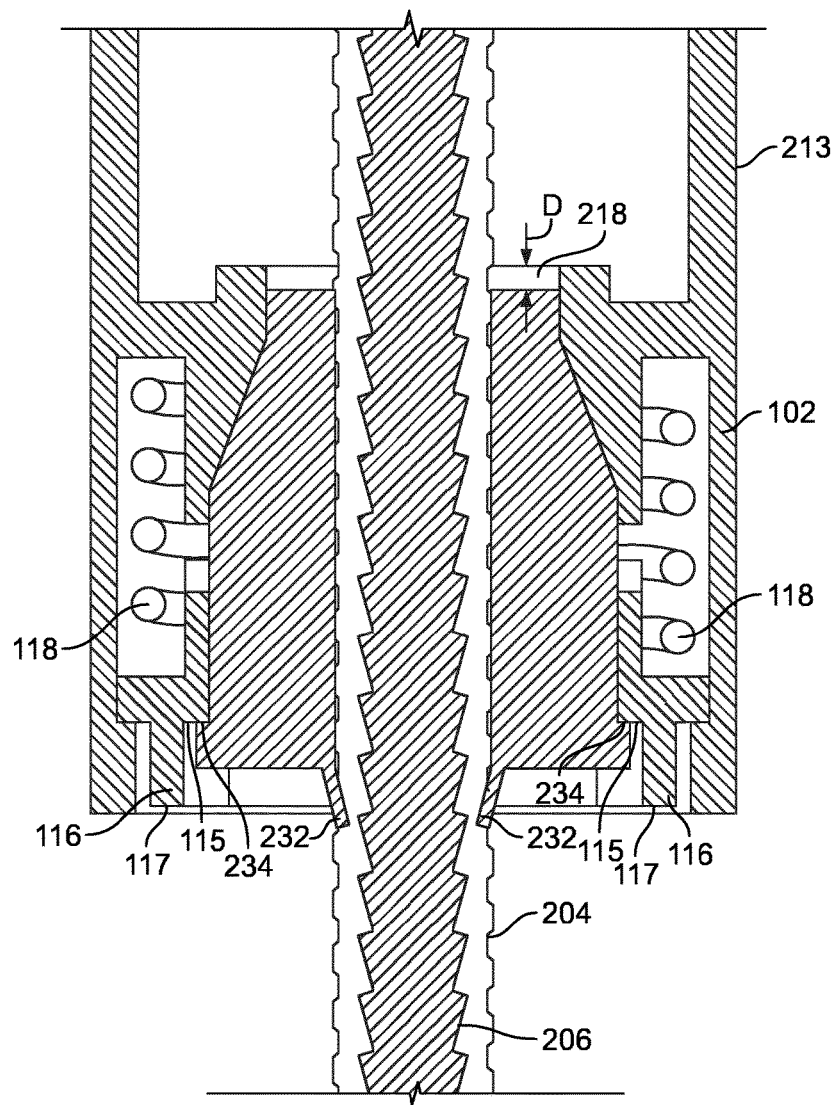
FIG. 8 is a cross-sectional view of the alternative reusable pen type medication dispensing apparatus illustrated in FIGS. 7A and B with cartridge housing removed from the pen type medication dispensing apparatus.

FIG. 8 illustrates the modified pen injection device 202 of FIGS. 7A and B with the cartridge holder removed. As illustrated, after the cartridge holder has been removed from the modified dose setting mechanism 213, the cartridge no longer pushes upon the clutch engaging surface 117. This allows the cartridge or clutch spring 118 to expand and will therefore act to drive the clutch 116 distally. As the spring 118 pushed the clutch 116 distally, a bottom shoulder of the clutch 116 engages the modified lead screw guide bottom ledge 234 and hence the modified lead screw guide 224 in the distal direction, towards the injection site. This distance D 218 is noted in FIG. 8. As this allows distal movement of the modified lead screw guide 224, the lead screw 204 under the force of the spring 118 allows the lead screw guide 224 to reach its end position as illustrated in FIG. 8. As such, the lead screw guide 224 no longer resides in a compressed state and can now expand or open up, thereby disengaging the lead screw guide ratchet arms 232 from the lead screw teeth 206 of the modified lead screw 204. The modified lead screw 204 can now be moved in the proximal direction so that the dose setting mechanism 213 can be reset for further use.

In an alternative embodiment of the assembly, which is not explicitly indicated in the Figures, allows the ratchet arms to be arranged radially such that not only the lead screw is axially moveable but also the lead screw guide is rotatable with respect to the lead screw, e.g., such that the lead screw guide need not necessarily be rotated, e.g. with respect to the housing, when the lead screw is being reset. To this effect, the ratchet arms are expediently radially moved out of the cross-sectional portion of the lead screw.

Figure 9A:
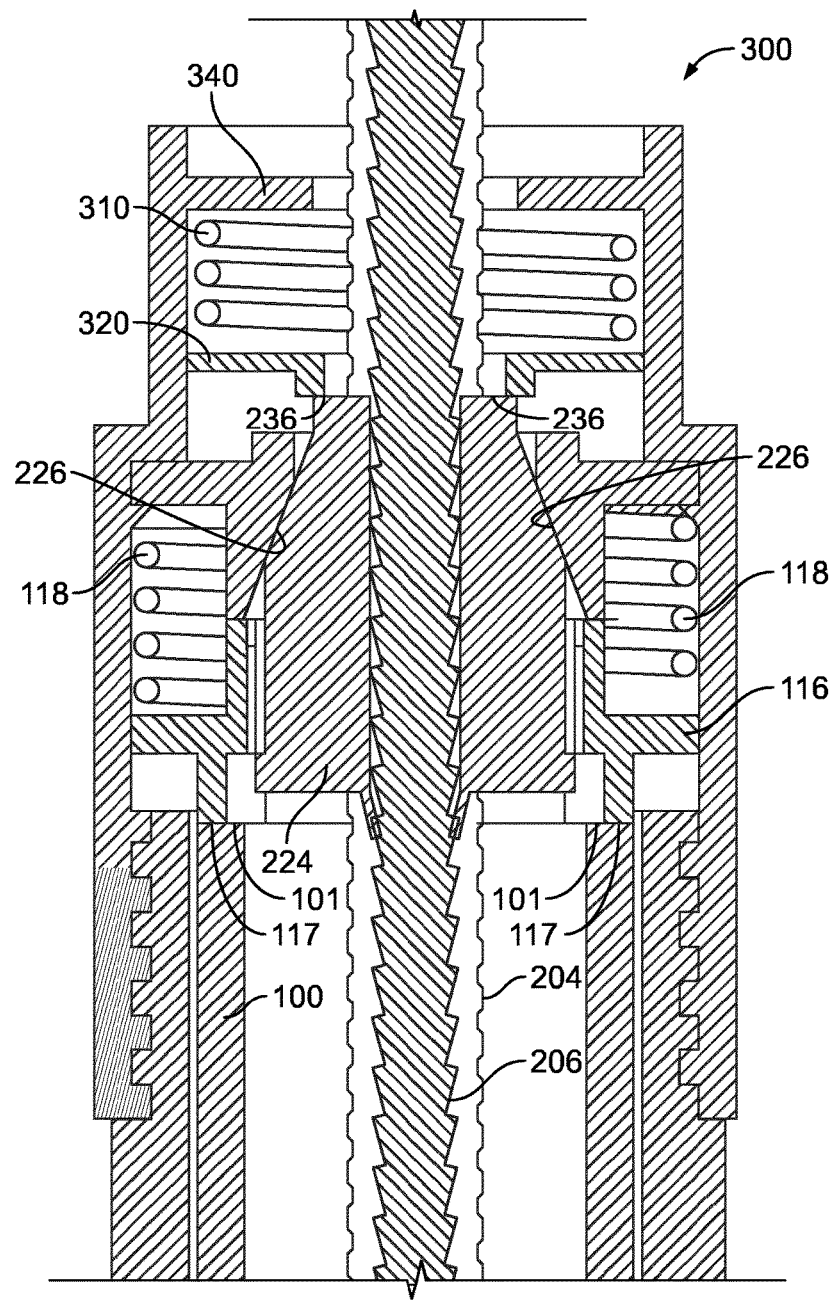
FIG. 9A is a cross-sectional view of a portion of yet another alternative reusable pen type medication dispensing apparatus utilizing the modified lead screw guide of FIG. 6 with an attached cartridge housing.
Figure 9B:
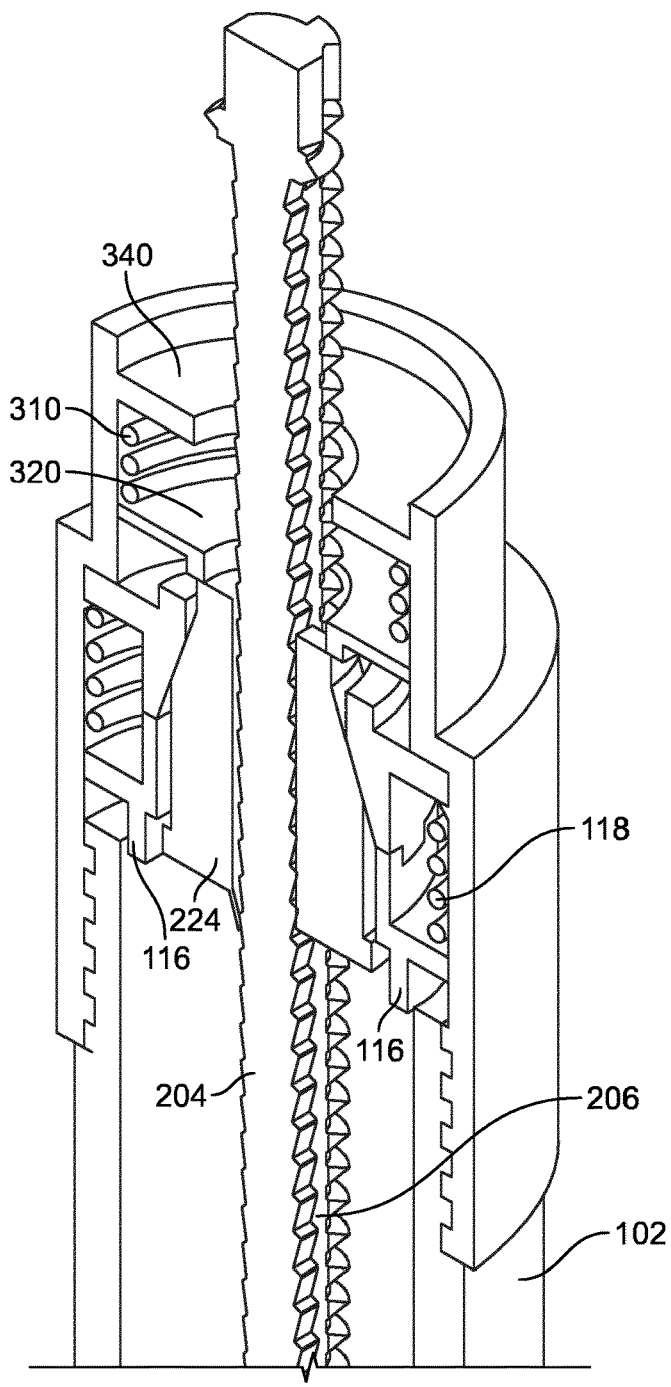
FIG. 9B is an alternative cross-sectional view of a portion of the alternative reusable pen type medication dispensing apparatus illustrated in FIG. 9A.

FIG. 9A is a cross-sectional view of a portion of yet another alternative reusable pen type medication dispensing apparatus or device 300 utilizing the modified lead screw guide of FIG. 6 with an attached cartridge housing. FIG. 9B is an alternative cross-sectional view of the alternative reusable pen type medication dispensing apparatus 300 illustrated in FIG. 9A. The pen type dispensing apparatus 300 is similar in configuration to the pen type injection device 200 illustrated in FIGS. 7-8. However, one difference is that this reusable device 300 further comprises a plate spring 310 and a plate 320. The spring plate 320 is configured to reside on a proximal bearing surface 236 of the modified lead screw guide 224. The plate spring 310 resides in a compressed state between an inner housing portion 340 and the spring plate 320.

As shown in FIGS. 9A and 9B, the cartridge 100 contained within the cartridge holder 114 pushes upon the clutch surface 117. The clutch 116 pushes the lead screw guide 224 into its seated end position with the proximal end face 236 of the lead crew guide 224 abutting a bottom surface of the spring plate 320, similar to the lead screw guide configuration illustrated in FIGS. 7-8. According to this alternative, the lead screw guide may e.g. be made of an intrinsically elastic material.

Figure 10A:
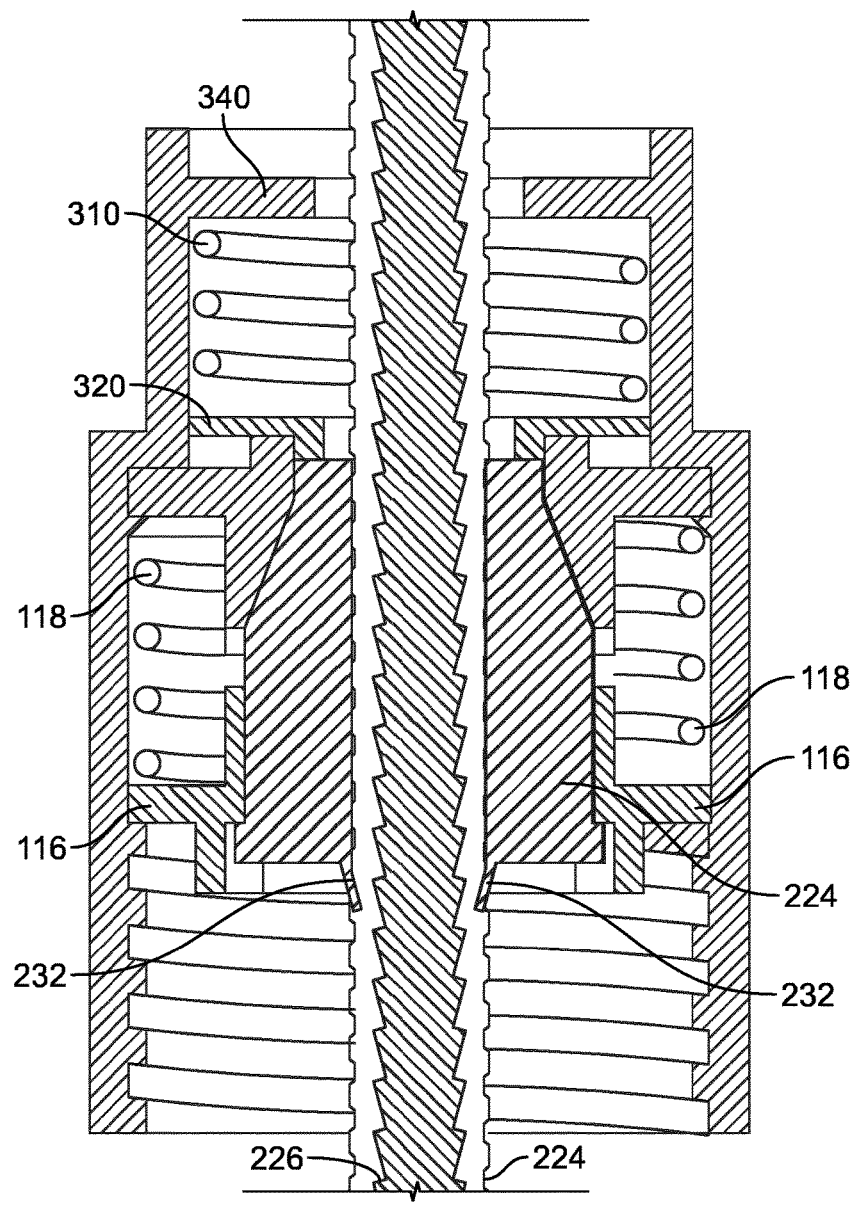
FIG. 10A is a cross-sectional view of the alternative reusable pen type medication dispensing apparatus illustrated in FIG. 9 with cartridge housing removed from the pen type medication dispensing apparatus.
Figure 10B:
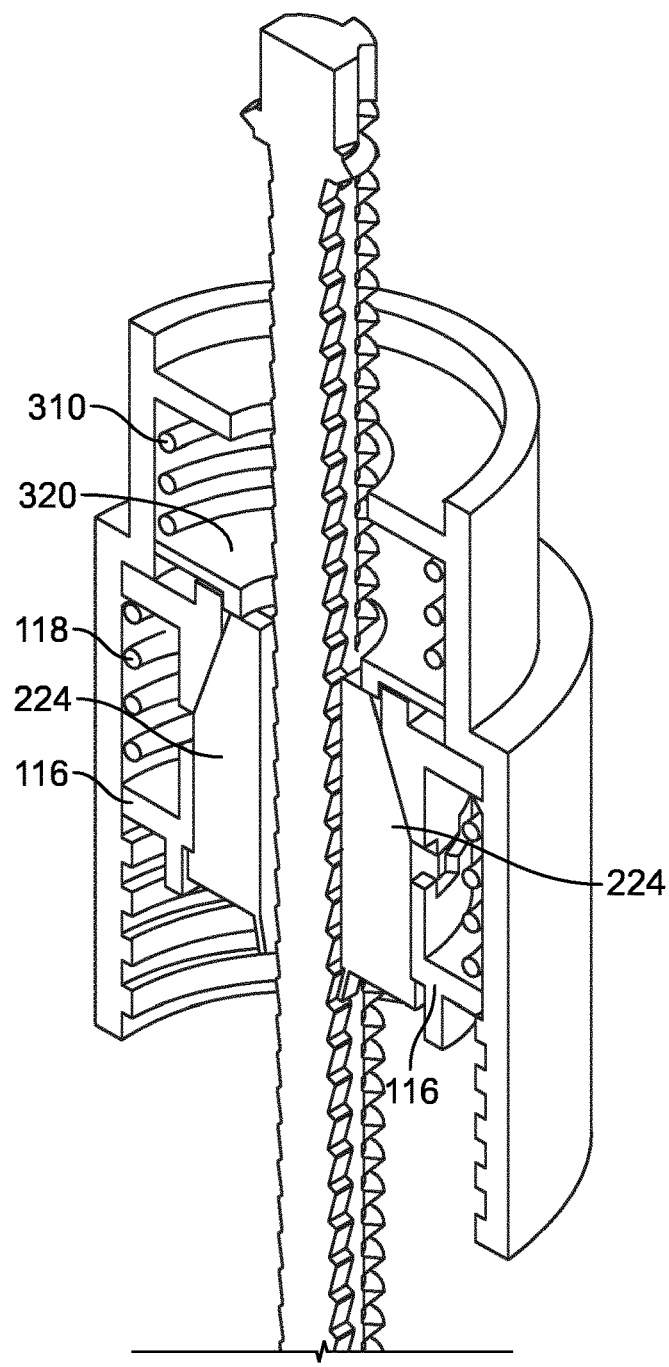
FIG. 10B is an alternative cross-sectional view of the alternative reusable pen type medication dispensing apparatus illustrated in FIG. 10A.

FIG. 10 is a cross-sectional view of the alternative reusable pen type medication dispensing apparatus 300 illustrated in FIG. 9 with the cartridge holder 114 removed from the pen type medication dispensing apparatus. As illustrated, removal of the cartridge holder 114 allows the clutch 116 to move in the distal direction under the force of the cartridge spring 118. In addition, the plate spring 310 will also then push upon the plate 320. This spring plate 320 will also assist in pushing the modified lead screw guide 224 to its end position. The modified lead screw guide 224 moves axially and thereby opening the interaction between the lead screw ratchet teeth 206 and the modified lead screw 204. As such, the modified lead screw 204 can be moved both in the distal direction as well as in the proximal direction.

The lead screw may be generically embodied as a piston rod. The lead screw guide may be generically embodied as a piston rod guide. The dial link may be a dose member. The number sleeve may be generically embodied as an indication member. The mid-body and/or the housing shoulder be a further component, e.g. of the housing or rigidly fixed to the housing. The clutch may relate to a clutch element. The ratchet arm may be generically embodied as a guide interaction feature. The teeth, particularly the lead screw ratchet arm engaging teeth may be Generically embodied as a piston rod interaction feature. The plate spring may be generically embodied as a spring element. The flexible compressible spring part may further be generically embodied as a compressible member.

The terms "medicament", "drug" or "medicinal product", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2, H(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ, and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

While this invention has been shown and described as having various designs, the present invention may be modified within the spirit and scope of this disclosure. For example, to deliver a fixed dose, the pen would preferably be modified such that the maximum that the dial could be screwed out to prepare the pen for injection would correspond to the fixed dose. Such a fixed dose pen could eliminate numerical dosage indicating marking, and instead provide user cues in the form of, for example, instructions and a graphical dosing indicator. This disclosure is therefore intended to cover any variations, uses or adaptations of the invention using its general principles. Further, this disclosure is intended to cover such departures from the present disclosure as come within known or customary practice in the art to which this invention pertains.

The invention claimed is:

1. An assembly for a drug delivery device, the assembly comprising:
   a housing;
   a piston rod having a longitudinal axis, a distal end and a proximal end, the piston rod further comprising a piston rod interaction feature, the piston rod interaction feature comprising a plurality of ratchet teeth; and
   a piston rod guide being movable with respect to the piston rod, the piston rod guide further comprising a guide interaction feature corresponding to the piston rod interaction feature, the guide interaction feature comprising a ratchet arm, and the piston rod guide being movable with respect to the piston rod to switch between a first state and a second state of the assembly, the second state being different from the first state,
   wherein the assembly is configured such that, in the first state of the assembly, the piston rod guide is in a first axial position relative to the piston rod in which the piston rod interaction feature is arranged to interact with the guide interaction feature to prevent proximal movement of the piston rod with respect to the housing, and wherein, in the second state of the assembly, the piston rod guide is in a second axial position relative to the piston rod, the second axial position being different from the first axial position, wherein, in the second axial position, the piston rod interaction feature and the guide interaction feature are arranged such that proximal movement of the piston rod with respect to the housing is allowed,
   wherein the assembly comprises a spring element configured to move an entirety of the piston rod guide from the first axial position to the second axial position along the piston rod, and
   wherein the spring element is an integral part of the piston rod guide, wherein the assembly is configured such that, in the first state of the assembly, the spring element tends to move the guide interaction feature from a first radial position to a second radial position.

2. The assembly of claim 1, wherein the assembly is configured such that, in the first state of the assembly, the piston rod is rotationally fixed to the piston rod guide, and wherein, in the second state of the assembly, the piston rod is either rotationally fixed to the piston rod guide or rotatable with respect to the piston rod guide.

3. The assembly of claim 1, wherein the piston rod interaction feature and the guide interaction feature are designed to form a unidirectional axial coupling between the piston rod and the piston rod guide in the first state of the assembly.

4. The assembly of claim 1, wherein the assembly comprises a reservoir, the assembly is configured such that the reservoir can be releasably coupled to remainder of the assembly and, in the first state of the assembly, the reservoir is coupled to the remainder of the assembly and in the second state, the reservoir is decoupled from the remainder of the assembly, and the piston rod is resettable towards a proximal initial position.

5. The assembly of claim 1, wherein the assembly is configured such that, in the first state of the assembly, the guide interaction feature is in the first radial position with respect to the piston rod, and wherein in the second state of the assembly, the guide interaction feature is in the second radial position with respect to the piston rod, the second radial position being further away from the piston rod than the first radial position.

6. The assembly of claim 1, wherein the piston rod extends through a guiding opening of the piston rod guide, and wherein the assembly is configured such that, in the second state of the assembly, the guiding opening of the piston rod guide is radially enlarged as compared to the first state of the assembly.

7. The assembly of claim 1, wherein the piston rod guide comprises a first part and a second part, wherein the first and second parts are connected with each other via a flexible resilient spring part forming the spring element, and wherein the assembly is configured such that, during a switch from the first state to the second state, a radial movement of the first and the second part is converted into an axial movement of the piston rod guide.

8. The assembly of claim 1, wherein the piston rod guide comprises a guide portion rotationally locking the piston rod in the first state of the assembly, wherein the assembly is configured such that, in the second state of the assembly, the piston rod guide is rotationally fixed relative to the housing, and wherein the guide portion of the piston rod guide is radially arranged such that the piston rod is rotatable with respect to the piston rod guide.

9. An assembly for a drug delivery device, the assembly comprising:
   a housing;
   a piston rod having a longitudinal axis, a distal end and a proximal end, the piston rod further comprising a piston rod interaction feature, the piston rod interaction feature comprising a plurality of ratchet teeth, and
   a piston rod guide being movable with respect to the piston rod, the piston rod guide further comprising a guide interaction feature corresponding to the piston rod interaction feature, the guide interaction feature comprising a ratchet arm, and the piston rod guide being movable with respect to the piston rod to switch between a first state and a second state of the assembly, the second state being different from the first state,
   wherein the assembly is configured such that, in the first state of the assembly, the piston rod guide is in a first axial position relative to the piston rod in which the piston rod interaction feature is arranged to interact with the guide interaction feature to prevent proximal movement of the piston rod with respect to the housing, and wherein, in the second state of the assembly, the piston rod guide is in a second axial position relative to the piston rod, the second axial position being different from the first axial position, wherein, in the second axial position, the piston rod interaction feature and the guide interaction feature are arranged such that proximal movement of the piston rod with respect to the housing is allowed,
   wherein the assembly comprises a spring element, and wherein, in the first state of the assembly, the spring element tends to move the piston rod guide from the first axial position to the second axial position, and
   wherein the piston rod guide is elastically deformable and the spring element is a part separate from the piston rod guide, wherein, in the first axial position of the piston rod guide, the piston rod guide is elastically deformed, and, in the second axial position of the piston rod guide, the piston rod guide is relaxed.

10. The assembly of claim 9, wherein the assembly is configured such that, in the first state of the assembly, the piston rod is rotationally fixed to the piston rod guide, and wherein, in the second state of the assembly, the piston rod is either rotationally fixed to the piston rod guide or rotatable with respect to the piston rod guide.

11. The assembly of claim 9, wherein the piston rod interaction feature and the guide interaction feature are designed to form a unidirectional axial coupling between the piston rod and the piston rod guide in the first state of the assembly.

12. The assembly of claim 9, wherein the assembly comprises a reservoir, the assembly is configured such that the reservoir can be releasably coupled to a remainder of the assembly and, in the first state of the assembly, the reservoir is coupled to the remainder of the assembly and in the second state, the reservoir is decoupled from the remainder of the assembly, and the piston rod is resettable towards a proximal initial position.

13. The assembly of claim 9, wherein the assembly is configured such that, in the first state of the assembly, the guide interaction feature is in a first radial position with respect to the piston rod, and wherein in the second state of the assembly, the guide interaction feature is in a second radial position with respect to the piston rod, the second radial position being further away from the piston rod than the first radial position.

14. The assembly of claim 9, wherein the piston rod extends through a guiding opening of the piston rod guide, and wherein the assembly is configured such that, in the second state of the assembly, the guiding opening of the piston rod guide is radially enlarged as compared to the first state of the assembly.

15. The assembly of claim 9, wherein the piston rod guide comprises a first part and a second part, wherein the first and second parts are connected with each other via a flexible resilient spring part, and wherein the assembly is configured such that, during a switch from the first state to the second state, a radial movement of the first and the second part is converted into an axial movement of the piston rod guide.

16. The assembly of claim 9, wherein the piston rod guide comprises a guide portion rotationally locking the piston rod in the first state of the assembly, wherein the assembly is configured such that, in the second state of the assembly, the piston rod guide is rotationally fixed relative to the housing, and wherein the guide portion of the piston rod guide is radially arranged such that the piston rod is rotatable with respect to the piston rod guide.

17. The assembly of claim 9, further comprising:
a clutch mechanism, wherein the assembly is configured such that, in the first state of the assembly, the clutch mechanism is engaged and rotationally fixes the piston rod guide relative to the housing, and, in the second state of the assembly, the clutch mechanism is released and the piston rod guide is rotatable relative to the housing.

18. The assembly of claim 17, wherein the clutch mechanism comprises a clutch spring, a clutch member which is axially movable with respect to the housing and a further component, wherein either the clutch member or the further component contacts the piston rod guide in order to engage the clutch mechanism.

19. The assembly of claim 9, wherein the piston rod comprises a thread and the assembly further comprises:
a drive nut being threadedly engaged and screwable along the thread of the piston rod,
an indication member being threadedly engaged with the housing to be screwable relative to the housing;
a dose member connected with the drive nut and being axially movable and rotatably fixed relative to the drive nut, the dose member being rotatably fixed with the indication member when the dose member and the indication member are in a first axial arrangement, and the indication member being rotatable relative to the dose member when the dose member and the indication member are in a second axial arrangement; and
an inner sleeve being threadedly engaged with the indication member, the inner sleeve being axially movable and rotatably fixed relative to the housing.

20. A drug delivery device comprising the assembly of claim 9.

* * * * *

UNITED STATES PATENT AND TRADEMARK OFFICE
CERTIFICATE OF CORRECTION

PATENT NO. : 10,537,684 B2
APPLICATION NO. : 15/037339
DATED : January 21, 2020
INVENTOR(S) : Stefan Blancke et al.

Page 1 of 1

It is certified that error appears in the above-identified patent and that said Letters Patent is hereby corrected as shown below:

In the Claims

In Column 27, Line 12, Claim 4, after "to" insert -- a --

Signed and Sealed this
Seventh Day of April, 2020

Andrei Iancu
*Director of the United States Patent and Trademark Office*